(12) United States Patent
McWeeney et al.

(10) Patent No.: US 11,207,172 B2
(45) Date of Patent: Dec. 28, 2021

(54) STENT DESIGNS TO COVER CATHETER ACCESS SITE

(71) Applicant: Covidien LP, Mansfield, MA (US)

(72) Inventors: John O. McWeeney, Brighton, MA (US); Hillary K. Huszar, Redwood City, CA (US); Mark A. Maguire, Hillsborough, CA (US); Shawn C. Daniel, San Jose, CA (US); Scott Bartfield, Weston, MA (US); Brian Tinkham, Scituate, MA (US); David H. Hamilton, Newmarket (CA); David J. Karasek, Waukesha, WI (US)

(73) Assignee: Covidien LP, Mansfield, MA (US)

( * ) Notice: Subject to any disclaimer, the term of this patent is extended or adjusted under 35 U.S.C. 154(b) by 82 days.

(21) Appl. No.: 16/242,587

(22) Filed: Jan. 8, 2019

(65) Prior Publication Data

US 2020/0214861 A1 Jul. 9, 2020

(51) Int. Cl.
*A61F 2/04* (2013.01)
*A61F 2/07* (2013.01)
(Continued)

(52) U.S. Cl.
CPC .............. *A61F 2/04* (2013.01); *A61F 2/07* (2013.01); *A61F 2/844* (2013.01); *A61F 2/966* (2013.01); *A61F 2/90* (2013.01); *A61F 2/91* (2013.01); *A61F 2002/045* (2013.01); *A61F 2002/823* (2013.01); *A61F 2210/0014* (2013.01); *A61F 2210/0057* (2013.01); *A61F 2220/0091* (2013.01); *A61F 2250/0006* (2013.01);
(Continued)

(58) Field of Classification Search
CPC ........... A61F 2/04–2002/075; A61F 2/82–945; A61F 2220/0091
See application file for complete search history.

(56) References Cited

U.S. PATENT DOCUMENTS

2001/0014794 A1* 8/2001 Moll ..................... A61B 17/11
604/289
2012/0172929 A1 7/2012 Shalev
(Continued)

FOREIGN PATENT DOCUMENTS

EP 3679902 A3 9/2020

OTHER PUBLICATIONS

Extended European Search Report—20150480.0—dated Aug. 14, 2020.

*Primary Examiner* — Rebecca S Preston
(74) *Attorney, Agent, or Firm* — Holland & Hart LLP

(57) ABSTRACT

Methods, apparatuses and systems are described for delivering a stent through an access hole of a body lumen and covering up the access hole after deploying the stent, Stents are described that include a stent body defining a body lumen contact surface area and a deployable member configured to deploy from the stent body and increase the body lumen contact surface area of the stent. Deployable members that hinge, unroll, extend, expand, and coaxially translate with respect to the stent body are described. A system for delivering a stent into a body lumen are described that may include a coverage member configured to at least partially cover the hole in the wall of the stent upon withdrawing a tubular member through the hole in the wall of the stent. Coverage members may include a self-sealing membrane, a flap valve, or a hinged valve.

5 Claims, 21 Drawing Sheets

(51) Int. Cl.
*A61F 2/966* (2013.01)
*A61F 2/844* (2013.01)
*A61F 2/91* (2013.01)
*A61F 2/82* (2013.01)
*A61F 2/90* (2013.01)

(52) U.S. Cl.
CPC .............. *A61F 2250/0039* (2013.01); *A61F 2250/0065* (2013.01); *A61F 2250/0069* (2013.01)

(56) References Cited

U.S. PATENT DOCUMENTS

| | | | |
|---|---|---|---|
| 2012/0203339 A1* | 8/2012 | Heaven | A61F 2/0811 623/13.14 |
| 2012/0253387 A1 | 10/2012 | Teichman et al. | |
| 2013/0197657 A1 | 8/2013 | Anca et al. | |
| 2014/0066979 A1 | 3/2014 | Jonsson | |
| 2016/0242940 A1* | 8/2016 | Krautkremer | A61F 2/848 |
| 2019/0209320 A1* | 7/2019 | Drasler | A61F 2/2418 |

* cited by examiner

STENT DESIGNS TO COVER CATHETER ACCESS SITE

BACKGROUND

Diseases and disorders of the gallbladder, pancreas, and bile ducts (i.e., pancreaticobiliary system) are associated with significant morbidity, mortality, and impaired quality of life. Obstructions, tumors, injuries, leakages, inflammation, infection and lesions can occur in these structures, which can eventually lead to conditions such as biliary colic, cholecystitis, choledocholithiasis, cholelithiasis, pancreatitis, pancreatic duct stone formations, and chronic abdominal pain. Diseases of the pancreaticobiliary system may also be associated with nutritional disorders, such as malnutrition, obesity, and high cholesterol.

To treat a biliary obstruction, a standard endoscopic retrograde cholangiopancreatography (ERCP) procedure may be performed. In general, a standard ERCP procedure includes placing an endoscope down the esophagus, through the stomach, and into the duodenum. A guide wire is then deployed from the endoscope, through the major duodenal papilla, and into the common bile duct along the retrograde direction. Once the guide wire is in place, a stent or other treatment device may be advanced over the guide wire into the common bile duct to remove obstructions, biopsy tumors, or otherwise treat the biliary system.

In some instances, the bile duct is inaccessible from the duodenum using the standard retrograde approach, such as when the biliary obstruction is too large or otherwise difficult to pass through with a guide wire. The risk of causing pancreatitis by repeatedly prodding the major duodenal papilla with the guide wire is another reason the standard retrograde approach may be avoided. In other cases, duodenal access to the bile duct may be blocked or impeded. In these circumstances, an antegrade approach to treating the biliary obstruction may be used.

A particular antegrade approach, known as a "Rendezvous" procedure, involves using an EUS (Endoscopic Ultrasonography) endoscope to access the common bile duct above (i.e., retrograde to) the blockage and then directing a guide wire through the access site into the common bile duct, across the blockage along the antegrade direction, and through the papilla into the duodenum. The EUS endoscope is then withdrawn from the patient, leaving the guide wire in place, and is exchanged for a standard ERCP endoscope. Once the scope exchange is complete, the portion of the guide wire in the duodenum is grasped and pulled back up through the ERCP endoscope. The clinician may then deploy a stent or other treatment device over the guide wire in the retrograde direction into the common bile duct just as in a standard ERCP procedure.

Although the "Rendezvous" approach may be preferred over the standard ERCP procedure in certain instances, the "Rendezvous" approach is time consuming, requires a complex scope exchange, and often causes the clinician to lose guide wire placement. Therefore, there may be a need for improved methods of treating a biliary blockage when the standard ERCP procedure is infeasible.

SUMMARY

The described features generally relate to methods, devices, and systems for delivering a stent into a body lumen through an access hole and covering the access hole after deploying the stent. Stent delivery systems are described for delivering the stent through the access hole and deploying the stent within the body lumen. Stents may include a deployable member that deploys from the body of the stent to cover the access hole after the stent delivery system is withdrawn back through the access hole. The described stent delivery systems may be used to deliver a stent through the wall of the common bile duct for direct antegrade placement of the stent across the major duodenal papilla. A deployable member may deploy from the body of the stent to cover the access hole in the common bile duct after the stent delivery system is withdrawn to prevent bile from leaking into the surrounding tissue.

The deployable member is generally configured to deploy during or after the withdrawal of the stent delivery system through the access hole. In some examples, deploying the deployable member includes releasing the deployable member from a constrained configuration. Additionally or alternatively, deploying the deployable member may include pulling on the deployable member.

Various stent designs are provided for covering an access hole. In general, a stent includes a stent body that defines a body lumen contact surface area when deployed within the body lumen. A stent also includes a deployable member configured to deploy from the stent body to increase the body lumen contact surface area of the stent.

The deployable member may deploy from the stent body in a variety of ways. For example, the deployable member may hinge from inside the stent body to outside the stent body. The deployable member may unroll from inside the stent body to outside the stent body. In other examples, the deployable member is configured to extend in length axially in a direction away from the stent body. In yet other examples, the deployable member is configured to translate axially in a direction away from the stent body from inside the stent body to outside the stent body.

The deployable member may include at least one flap hingedly coupled with the stent body. Alternatively, the deployable member may include a plurality of flaps hingedly coupled with the stent body and equidistantly spaced around a circumference of the stent body. In other examples, the deployable member is an accordion tube coupled with an end of the stent body. The accordion tube may include one or more integrated spring elements. In some examples, the deployable member is a tubular body sized to fit inside the stent body of the stent. In yet other examples, the deployable member is a flexible sleeve.

Systems for delivering a stent into a body lumen are also described. In certain aspects, a system includes a stent, a stent delivery system configured to deliver the stent through an access site in a wall of the body lumen, a tubular member configured to retract the stent toward the access site such that a proximal portion of the stent at least partially covers the access site, wherein the stent is disposed onto the tubular member such that the tubular member extends inside the stent along a distal portion of the stent, extends through a hole in a wall of the stent, and extends outside of the stent along the proximal portion of the stent, and a coverage member configured to at least partially cover the hole in the wall of the stent upon withdrawing the tubular member through the hole in the wall of the stent.

In certain aspects, the coverage member may comprise a self-sealing membrane material disposed on an outer surface of the wall of the stent and configured to seal the hole in the wall of the stent upon withdrawing the tubular member through the hole in the wall of the stent. In some examples, the coverage member may comprise a flap valve configured to seal the hole in the wall of the stent upon withdrawing the tubular member through the hole in the wall of the stent. In certain aspects, the coverage member may comprise a hinged valve configured to hinge such that upon withdrawing the tubular member through the hole in the wall of the stent, the hinged valve hinges to at least partially cover the hole in the wall of the stent. The system may also include a polymer jacket disposed on an outer surface of a central portion of the stent, wherein the coverage member is coupled with the polymer jacket.

Certain embodiments of the present disclosure may include some, all, or none of the above advantages or features. One or more other technical advantages or features may be readily apparent to those skilled in the art from the figures, descriptions, and claims included herein. Moreover, while specific advantages or features have been enumerated above, various embodiments may include all, some, or none of the enumerated advantages or features.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The present disclosure is generally directed to placing a stent within a body lumen. In certain procedures described herein, to place a stent within a body lumen, the luminal wall is pierced and a stent delivery system is advanced through the hole (i.e., access hole) and positioned at the target site (e.g., across an obstruction). The stent is then deployed from the stent delivery system, and the stent delivery system is withdrawn back out of the lumen through the same hole. If the hole is not covered, fluid from the lumen may leak out into the surrounding tissue and organs, which may potentially cause serious discomfort or other medical complications.

Apparatuses, systems, and methods are described herein for covering the access hole after the stent delivery system is withdrawn from the body lumen. For example, stents are described that include one or more deployable members that deploy after the stent delivery system is withdrawn to cover the access hole. The deployable member may be initially stowed within the stent and configured to deploy from inside the stent once the stent delivery system is withdrawn. The stent delivery system may interact with the deployable member to deploy it by releasing it from a constrained configuration or pulling on it as it is withdrawn from the access hole.

In some cases, apparatuses, systems, and methods are described herein for covering a hole in a wall of the stent after the stent delivery system (e.g., the guidewire lumen and guidewire) are withdrawn from the body lumen. In such cases, the stent may include a coverage member configured to seal the hole in the wall of the stent. The coverage member may be an example of a flap valve, a hinged vale, or a self-sealing membrane.

Embodiments of the present disclosure are now described in detail with reference to the drawings. As used herein, the term "clinician" refers to a doctor, surgeon, nurse, or any other care provider and may include support personnel. The term "proximal" will refer to the portion of the device or component thereof that is closer to the clinician and the term 'distal" will refer to the portion of the device or component thereof that is farther from the clinician.

Figure 1A:
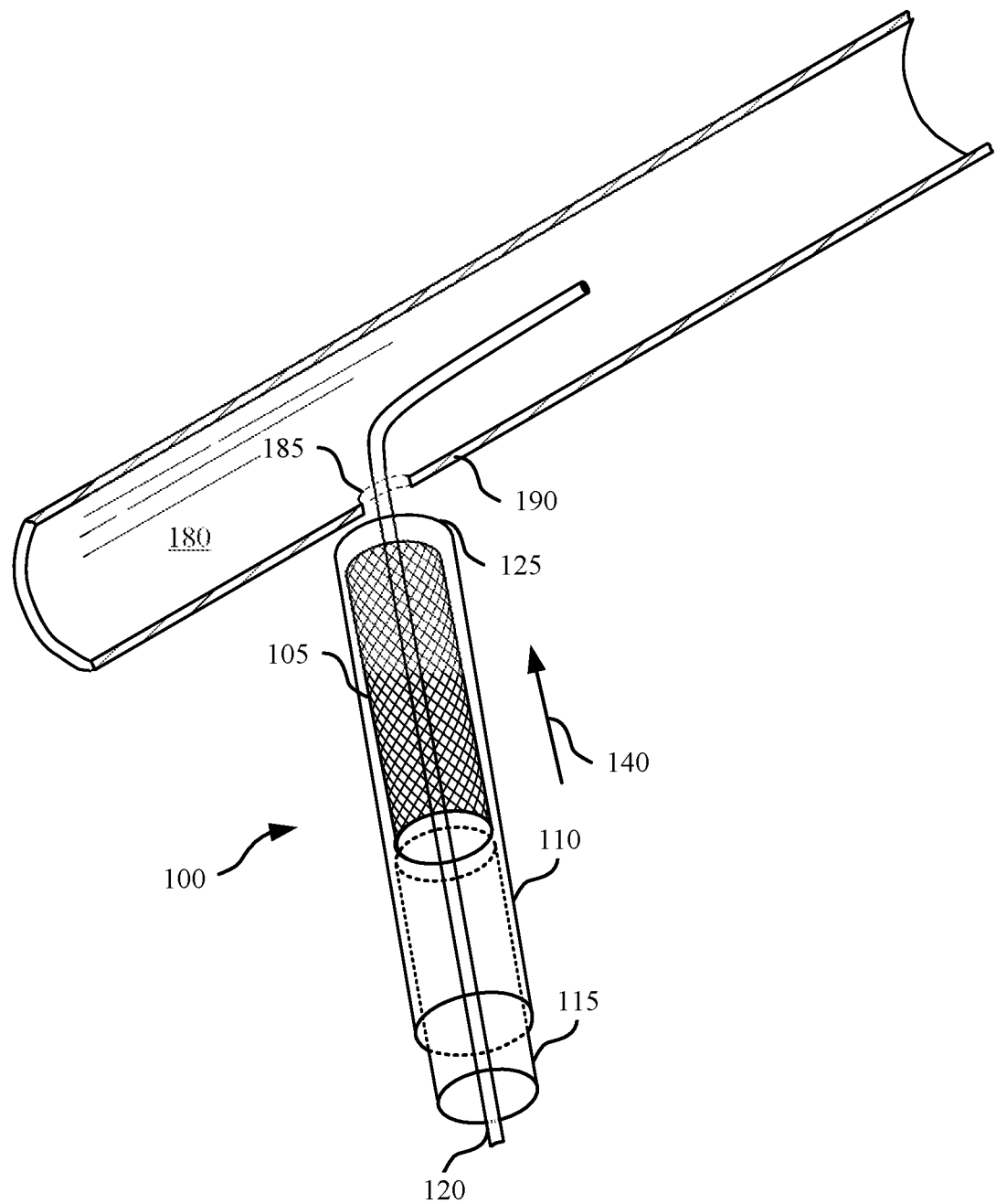
FIG. 1A illustrates a stent delivery system in accordance with aspects of the present disclosure.

FIG. 1A shows a stent delivery system 100 in accordance with aspects of the present disclosure. The stent delivery system 100 may be configured to place a stent 105 within a body lumen 180 to restore luminal flow across narrowed areas or blockages within the body lumen 180. The stent delivery system 100 may be sized or otherwise adapted to place a stent 105 within any body lumen 180, such as those associated with the pancreaticobiliary system, the arterial system, the bronchial system, the urinary system, or any other luminal system that may require stent treatment. The stent delivery system 100 generally includes an outer sheath 110 and a pusher 115. The guidewire lumen 120 may be part of the stent delivery system 100 or may be a separate component. The stent delivery system 100 can be provided as individual components, selectively combined components, or all together as a kit of components.

The outer sheath 110 is an elongate, tubular, flexible structure that is sized to provide a conduit through which the stent 105 travels to the target body lumen 180. The outer sheath 110 may access the human body through the working channel of an endoscope, for example. As will be appreciated, the outer sheath 110 may be made from any number of biocompatible materials or combinations of materials suitable for medical sheaths, catheters, and the like. The pusher 115 is sized to be advanced through the outer sheath 110 and is generally constructed from a flexible material with sufficient columnar strength to push the stent 105 from the distal end 125 of the outer sheath 110 into the body lumen 180. The pusher 115 may be a solid rod, or may include an internal lumen through which a guidewire lumen 120 may pass, as illustrated in FIG. 1A. Like the outer sheath 110, the pusher 115 may be made from any number of suitable materials for use in the human body.

In general, a stent 105 is a frame or scaffolding structure sized for placement within a body lumen 180 and configured to provide structural support to the inner surface of the body lumen 180. A stent 105 may be used to restore patency across narrowed or blocked areas within the body lumen 180 due to inflammation, tumors, plaque buildup, or any other obstructive feature. For example, as described in more detail with reference to FIGS. 10-11, a stent 105 may be placed across the major duodenal papilla to restore luminal flow through the common bile duct into the duodenum. Although references to the pancreaticobiliary system are provided herein, it should be appreciated that the stents 105 described herein may be used in any body lumen 180.

The stent 105 may be a self-expanding stent. In such examples, the stent 105 is radially compressed within the outer sheath 110 and will naturally expand to a larger circumference upon exiting the outer sheath 110. Alternatively, the stent 105 may require a balloon or similar expansion element to expand the stent 105 within the body lumen 180. In any case, the stent 105 is generally sized such that it contacts a fully circumferential inner surface of the body lumen 180 when expanded. The contact surface between the stent 105 and the inner surface of the body lumen 180 is referred to herein as the body lumen contact surface area.

The stent 105 may be made from any number of materials, combinations of materials, and constructions. For example, the stent 105 may be a braided stent made from a plurality of wires joined together in a cross-hatch configuration. The stent 105 depicted in FIGS. 1-7 and 9-11 are braided stents or at least include a stent body 135 that is braided. However, it should be appreciated that the stent 105 may be made from other stent constructions or combinations of stent constructions. In other examples, the stent 105 is a laser-cut stent formed from a single metallic tube with regions cut away for increased flexibility. In yet other examples, the stent 105 is a wire-form stent formed by one or more helically wrapped wires, as depicted in FIG. 8. It may be appreciated that the different stent constructions may exhibit particular characteristics such as radial expansive force, flexibility, reduced foreshortening, or migration resistance that may render a certain construction advantageous for a particular use. As described with reference to FIG. 8, a stent 105 may include some portions made from one stent construction (e.g., laser-cut) and another portion made from another stent construction (e.g., braided) to take advantage of the unique characteristics of each construction. In addition, as described with reference to FIG. 9, the radial expansion force exhibited by the stent 105 on the inner surface of the body lumen 180 may be varied along the length of the stent 105 to improve migration resistance and to provide structural support where it is needed most.

The individual wires or frame of the stent 105 may be made from any number of metallic materials including, but not limited to, titanium, nitinol, or stainless steel. It should be appreciated that other metallic or non-metallic materials may be used to construct the stent 105 that provide suitable flexibility, stiffness, and biocompatibility. The stent 105 may include a polymeric or fabric sleeve that covers some or all of the surface of the stent 105. Such a sleeve may protect the inner surface of the body lumen 180 from the bare metal of the stent 105 and may prevent tissue ingrowth. In some examples, the stent 105 is a drug-eluting stent.

Referring still to FIG. 1A, to place the stent delivery system 100 within the body lumen 180, an access site 185 is formed through the wall 190 of the body lumen 180, and the guidewire lumen 120 is then advanced through the access site 185 and into the body lumen 180. Systems, apparatuses, and methods for accessing a body lumen 180 and directing a guidewire lumen 120 into the body lumen 180 in a preferred direction are described in U.S. patent application Ser. No. 15/179,305, titled "Catheter With Pre-Formed Geometry for Endoscopic Ultrasound-Guided Access" commonly assigned to the assignee of the present application, the entire contents of which are incorporated herein.

Figure 1B:
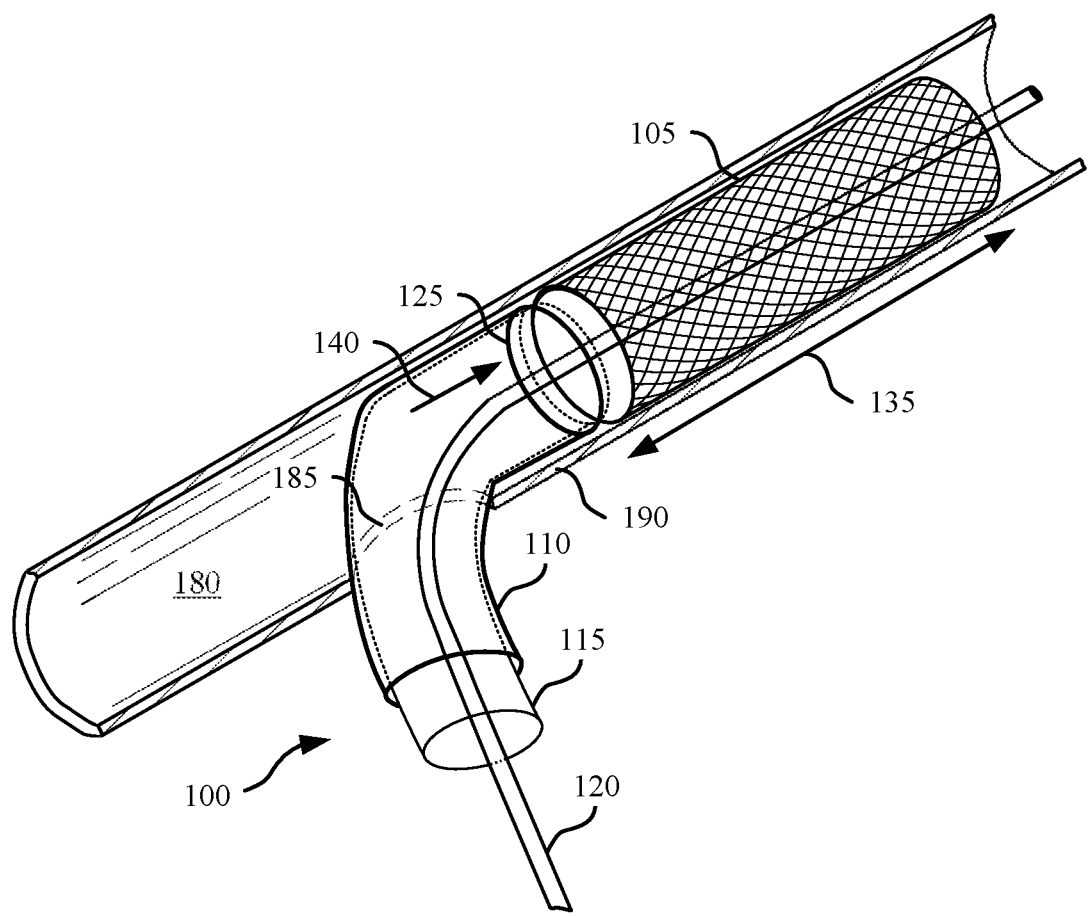
FIG. 1B illustrates a stent delivery system within a body lumen in accordance with aspects of the present disclosure.

Once the guidewire lumen 120 is in place, the outer sheath 110 is advanced distally, as indicated by arrow 140, over the guidewire lumen 120, through the access site 185, and into the body lumen 180. Advancing the outer sheath 110 through the access site 185 may dilate the access site 185 (as shown in FIG. 1B) beyond the initial size required to access the body lumen 180 with the guidewire lumen 120 (as shown in FIG. 1A). In some instances, the outer diameter of the outer sheath 110 may be as large as 10 F (3.33 mm) or larger. It may be appreciated that dilating the access site 185 may allow fluid to leak from the body lumen 180 into the surrounding tissue once the stent delivery system 100 is withdrawn from the body lumen 180, thereby potentially causing discomfort or other complications to the patient.

FIG. 1B shows the stent delivery system 100 of FIG. 1A within the body lumen 180 and with the stent 105 fully deployed. To deploy the stent 105 from the stent delivery system 100, the pusher 115 is advanced distally, as indicated by arrow 140, with respect to the outer sheath 110, or the outer sheath 110 is withdrawn proximally with respect to the pusher 115. Because the pusher 115 abuts against the stent 105, the stent 105 will be pushed from the distal end 125 of the outer sheath 110 as the pusher 115 is advanced distally or as the outer sheath 110 is withdrawn proximally. In the case of a self-expanding stent, the stent 105 expands to contact the inner surface of the body lumen 180 as it exits the outer sheath 110.

Figure 1C:
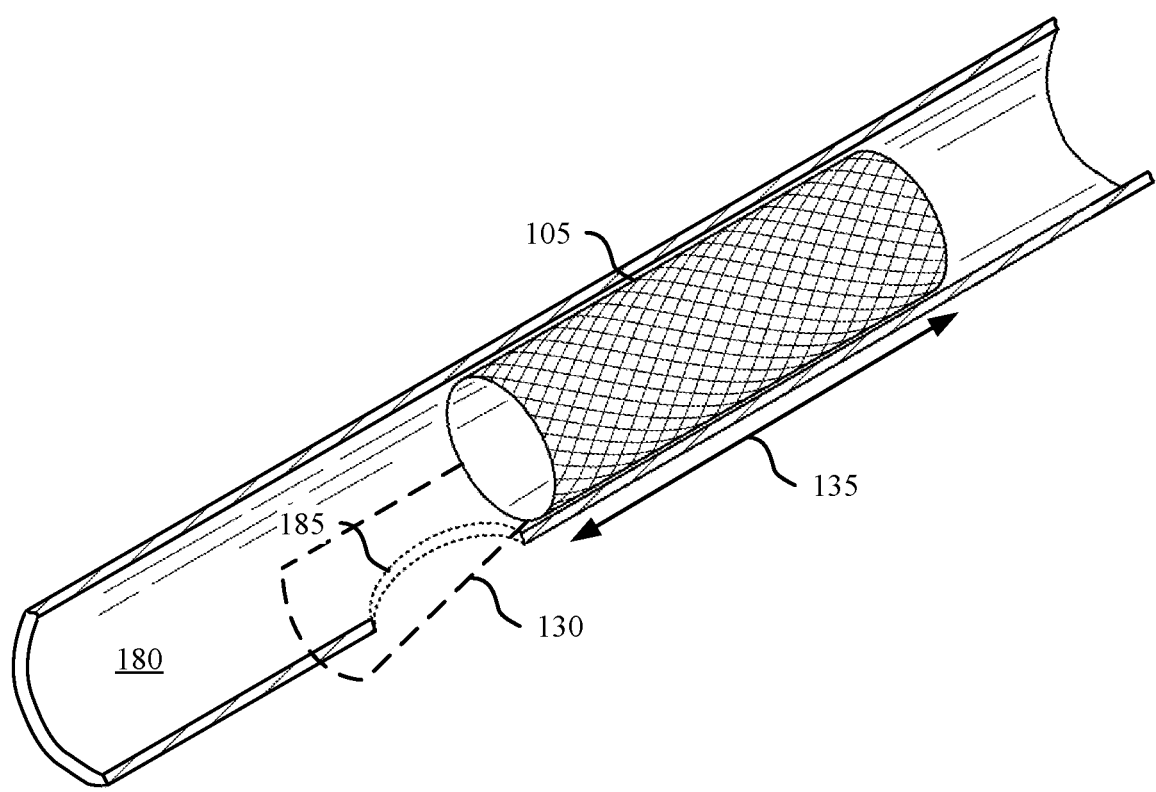
FIG. 1C illustrates a stent with a deployable member within a body lumen in accordance with aspects of the present disclosure.

FIG. 1C shows the stent 105 of FIGS. 1A-1B fully deployed within the body lumen 180 and with the stent delivery system 100 fully withdrawn from the body lumen 180. To withdraw the stent delivery system 100 after successful placement of the stent 105, the outer sheath 110 and the pusher 115 are withdrawn back through the access site 185. The guidewire lumen 120 is also withdrawn back through the access site 185 and can be done so before, after, or at the same time as the outer sheath 110 and pusher 115. After the stent delivery system 100 is withdrawn from the body lumen 180, liquid from the lumen 180 may leak into the surrounding tissue. In the case of the common bile duct, bile leakage into the surrounding tissue may cause serious discomfort to the patient.

To prevent or at least impede the flow of fluid from the body lumen 180, features of the stent 105 or stent delivery system 100 are configured to at least partially cover the access site 185. For example, the stent 105 may include a deployable member 130 that deploys from the stent body 135 of the stent 105 to cover the access site 185. In general, once deployed, the deployable member 130 increases the body lumen contact surface area of the stent 105. The deployable member 130 is generally coupled with the stent body 135 and remains attached to the stent body 135 after deployment. As described with reference to various figures, the deployable member 130 may deploy from the stent body 135 by hinging, unrolling, extending, expanding, or translating away from the stent body 135. The deployable member 130 may contact a partially circumferential portion of the body lumen 180 (as shown in FIG. 1C) or may instead contact a fully circumferential portion.

The deployable member 130 may include one or more separate elements that may be made from the same materials and construction as the stent body 135 or may instead be made from different materials or construction. For example, the deployable member 130 may include a frame or scaffolding structure like the stent body 135. If made from a frame or scaffolding structure, the deployable member 130 may include a covering or webbing that at least partially prevents liquid from flowing through the deployable member 130. Additionally or alternatively, the frame or scaffolding may be densely arranged (e.g., a mesh) to at least partially prevent the flow of liquid therethrough. In some cases, the deployable member 130 is a solid, unitary piece without a frame. The deployable member 130 may include materials with properties particularly suited for closing an access site 185 such materials that promote coagulation or healing, or materials that are absorbent or adherent.

The deployable member 130 may be triggered to deploy during or after the stent delivery system 100 is withdrawn back through the access site 185. In some examples, the deployable member 130 is constrained in a pre-deployed or stowed position by some component of the stent delivery system 100 or the stent 105, and by removing the stent delivery system 100 from the body lumen 180, the deployable member 130 is thereby unconstrained and will deploy to cover the access site 185. Additionally or alternatively, some component of the stent delivery system 100 may pull on or otherwise urge the deployable member 130 into the deployed position either during or after the stent delivery system 100 has been withdrawn from the body lumen 180.

Figure 2A:
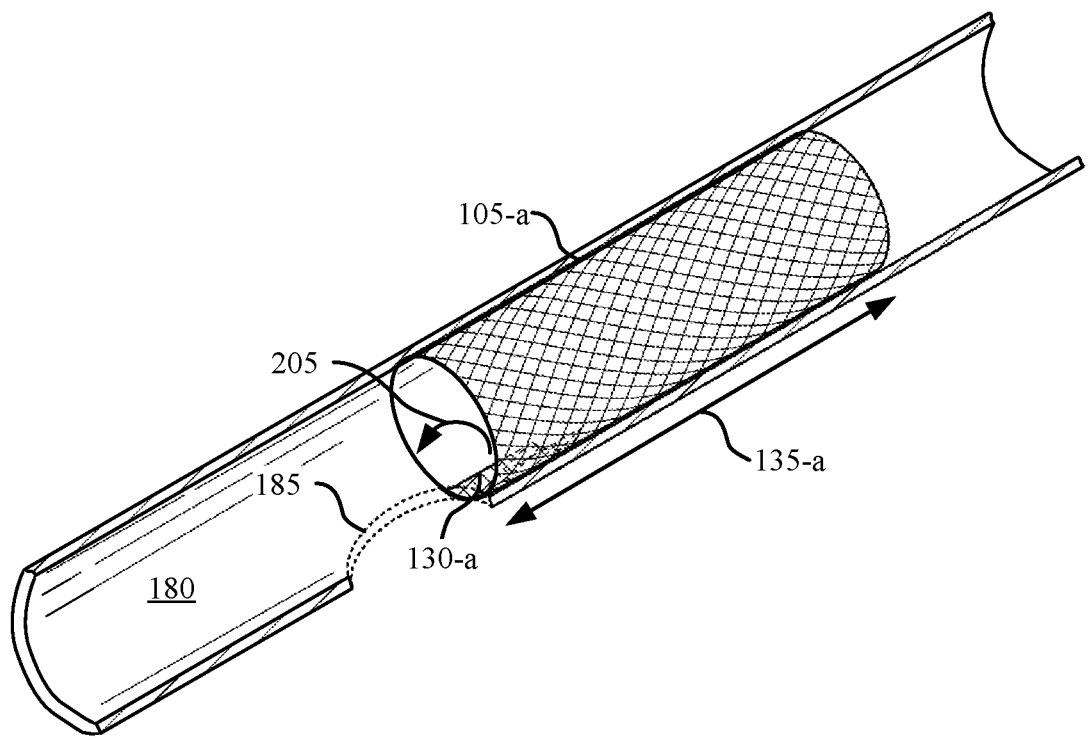
FIG. 2A illustrates a stent with a flap deployable member in a stowed configuration in accordance with aspects of the present disclosure.
Figure 2B:
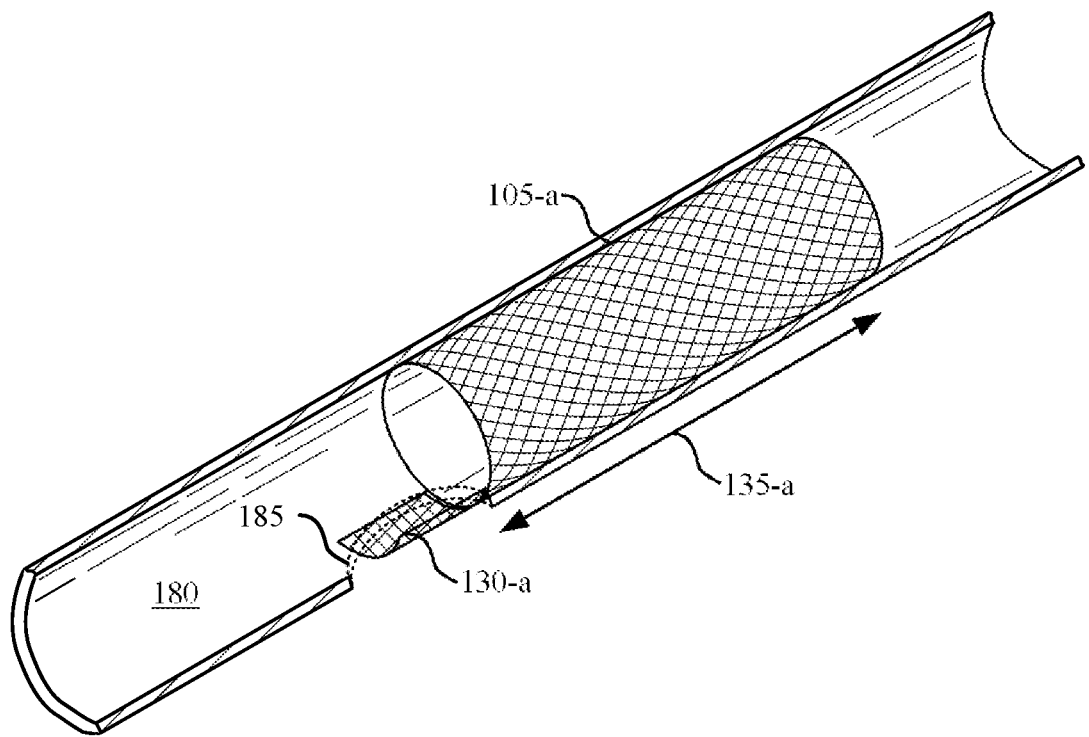
FIG. 2B illustrates a stent with a flap deployable member in a deployed configuration in accordance with aspects of the present disclosure.

FIG. 2A shows a fully deployed stent 105-*a* within a body lumen 180 in accordance with aspects of the present disclosure. The stent 105-*a* may be an example of the stent 105 of FIGS. 1A-1C. The stent 105-*a* includes a deployable member 130-*a* that is shown stowed within the stent body 135-*a*. The deployable member 130-*a* is a flap that is hingedly coupled with the stent body 135-*a*. The deployable member 130-*a* may deploy from the stem body 135-*a* by hinging, as indicated by arrow 205, from inside the stent body 135-*a* (as shown in FIG. 2A) to outside the stent body 135-*a* (as shown in FIG. 2B), thereby increasing the body lumen contact surface area of the stent 105-*a*. As such, the length of the deployable member 130-*a* is selected such that it clears the inner surface of the stent body 135-*a* as it hinges from inside to outside the stent body 135-*a*.

The deployable member 130-*a* may be configured to spring open to the deployed configuration shown in FIG. 2B when unconstrained. For example, the deployable member 130-*a* may be made from or include a material or component that stores elastic potential energy when in the stowed configuration. In such examples, some component of the stent delivery system 100 (e.g., the guidewire lumen 120 or the pusher 115) may hold the deployable member 130-*a* down in the stowed configuration while the stent delivery system 100 is still within the body lumen 180. As such, once the particular component is withdrawn from the body lumen 180, the deployable member 130-*a* is free to spring open to the deployed configuration shown in FIG. 2B.

Additionally or alternatively, the deployable member 130-*a* may be detachably connected with some component of the stent delivery system 100 by a pull string (e.g., a surgical suture). In such examples, as the stent delivery system 100 is withdrawn from the body lumen 180, the deployable member 130-*a* is pulled into the deployed configuration shown in FIG. 2B by the stent delivery system 100 as it exits the access site 185. Once the stent delivery system 100 is fully withdrawn from the body lumen 180, the connection between the stent delivery system 100 and the deployable member 130-*a* may be detached (e.g., breaking or otherwise disconnecting the pull string).

The deployable member 130-*a* may include a frame or other support structure and may be made from the same material or materials as the stent body 135-*a*. In other examples, the deployable member 130-*a* is made from a different material than the stent body 135-*a*. The materials forming the structure of the deployable member 130-*a* may be densely arranged (e.g., mesh-like) so as to impede the flow of fluid through the deployable member 130-*a*. The deployable member 130-*a* may also include a web, coating, or some other covering (e.g., silicon, polyurethane, polytetrafluoroetheylene, fabric) that prevents or at least impedes the flow of fluid therethrough.

Figure 3A:
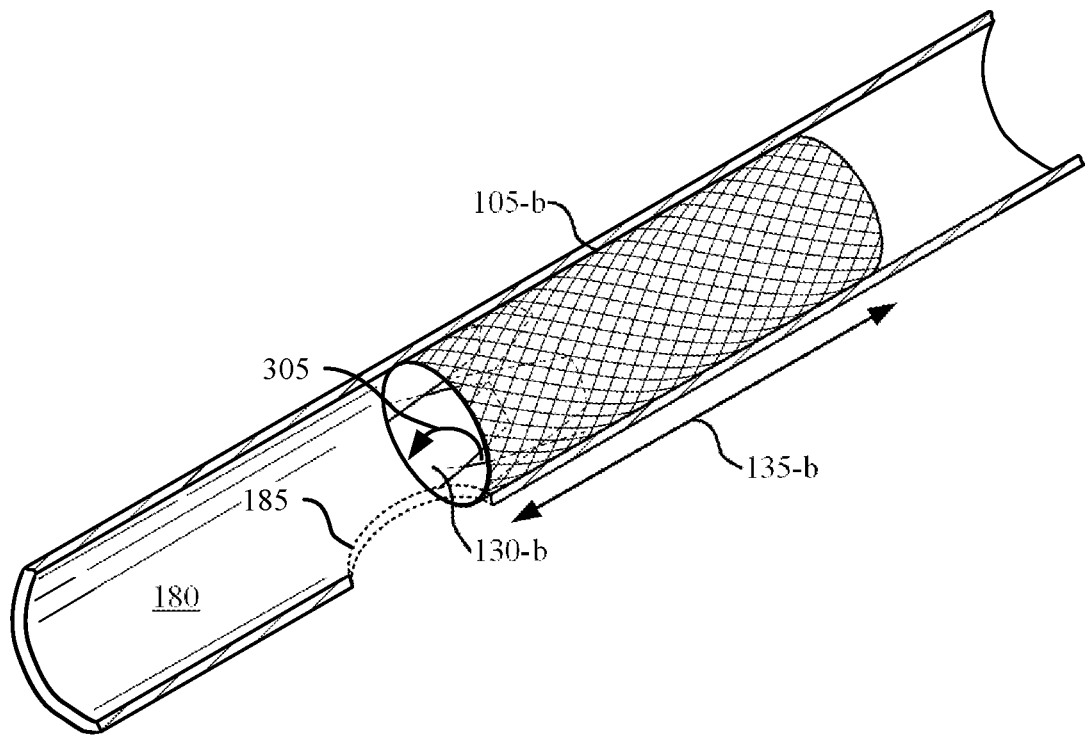
FIG. 3A illustrates a stent with a multi-flap deployable member in a stowed configuration in accordance with aspects of the present disclosure.

FIG. 3A shows a fully deployed stent 105-*b* within a body lumen 180 in accordance with aspects of the present disclosure. The stent 105-*b* may be an example of the stent 105 described with reference to FIGS. 1A-1C. The stent 105-*b* includes a deployable member 130-*b* that is shown stowed within the stent body 135-*b*. The deployable member 130-*b* includes a plurality of flaps that are hingedly coupled with the stent body 135-*b*. The individual flaps of the deployable member 130-*b* may be an example of or include features of the single flap of the deployable member 130-*a* described with reference to FIGS. 2A-2B. The individual flaps of the deployable member 130-*b* may deploy from the stent body 135-*b* by hinging, as indicated by arrow 305, from inside the stent body 135-*b* (as shown in FIG. 3A) to outside the stent body 135-*b* (as shown in FIG. 3B), thereby increasing the body lumen contact surface area of the stent 105-*b*.

The individual flaps of the deployable member 130-*b* may be equidistantly spaced around the circumference of the stent body 135-*b*. As such, once deployed, the deployable member 130-*b* provides coverage around a full circumference of the body lumen 180. Alternatively, the flaps may be spaced only around a partial circumference of the stent body 135-*b*. In such cases, the stent 105-*b* is radially aligned with respect to the body lumen 180 such that the deployable member 130-*b* covers the access site 185 when deployed. Depending on the number and size of the flaps of the deployable member 130-*b*, the flaps may at least partially overlap and therefore may deploy in serial fashion around the circumference of the stent body 135-*b*.

Figure 3B:
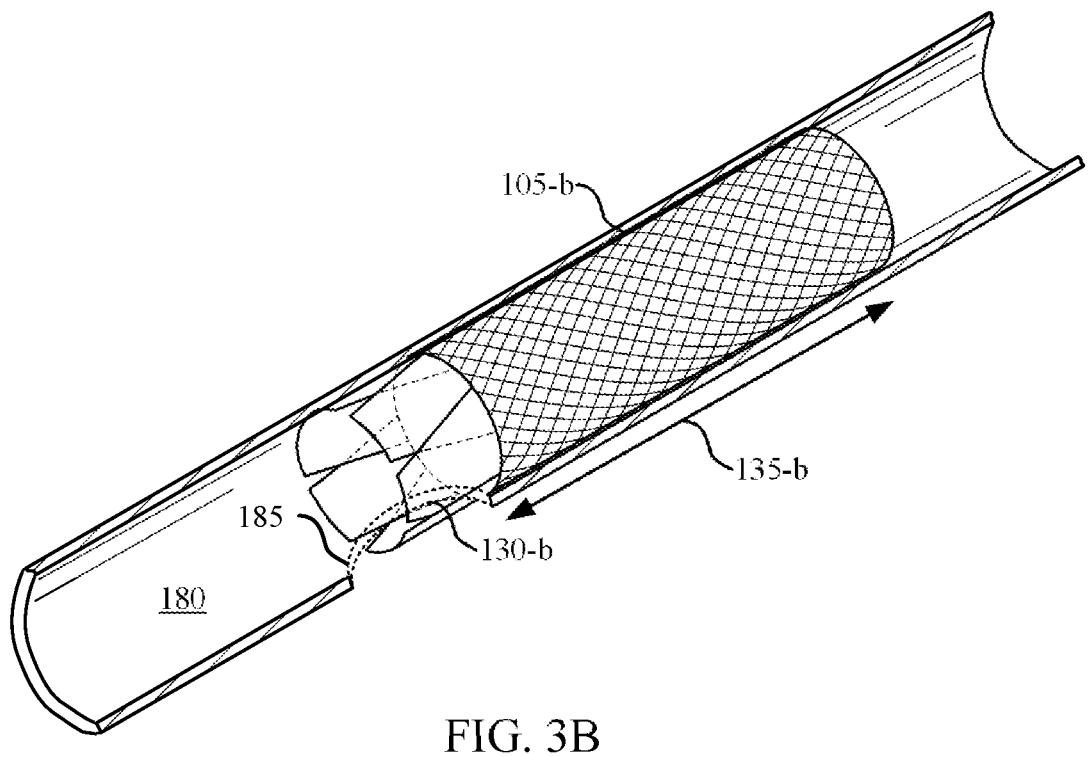
FIG. 3B illustrates a stent with a multi-flap deployable member in a deployed configuration in accordance with aspects of the present disclosure.

The deployable member 130-*b* may be configured to spring open to the deployed configuration shown in FIG. 3B when unconstrained. For example, the deployable member 130-*b* may be made from or include a material or component that stores elastic potential energy when in the stowed configuration. In such examples, some component of the stent delivery system 100 (e.g., the guidewire lumen 120 or the pusher 115) may hold the deployable member 130-*b* down in the stowed configuration while the stent delivery system 100 is still within the body lumen 180. As such, once the particular component is withdrawn from the body lumen 180, the deployable member 130-*b* is free to spring open to the deployed configuration shown in FIG. 3B.

Additionally or alternatively, the deployable member 130-*b* may be detachably connected with some component of the stent delivery system 100 by a pull string (e.g., a surgical suture). In such examples, as the stent delivery system 100 is withdrawn from the body lumen 180, the deployable member 130-*b* is pulled into the deployed configuration shown in FIG. 3B by the stent delivery system 100 as it exits the access site 185. Once the stent delivery system 100 is fully withdrawn from the body lumen 180, the connection between the stent delivery system 100 and the deployable member 130-*b* may be detached (e.g., breaking or otherwise disconnecting the pull string).

The individual flaps of the deployable member 130-*b* may include a frame or other support structure and may be made from the same material or materials as the stent body 135-*b*. In other examples, the deployable member 130-*b* is made from a different material than the stent body 135-*b*. The materials forming the structure of the deployable member 130-*b* may be densely arranged (e.g., mesh-like) so as to impede the flow of fluid through the deployable member 130-*b*. The deployable member 130-*b* may also include a web, coating, or some other covering (e.g., silicon, polyurethane, polytetrafluoroetheylene, fabric) that prevents or at least impedes the flow of fluid therethrough.

Figure 4A:
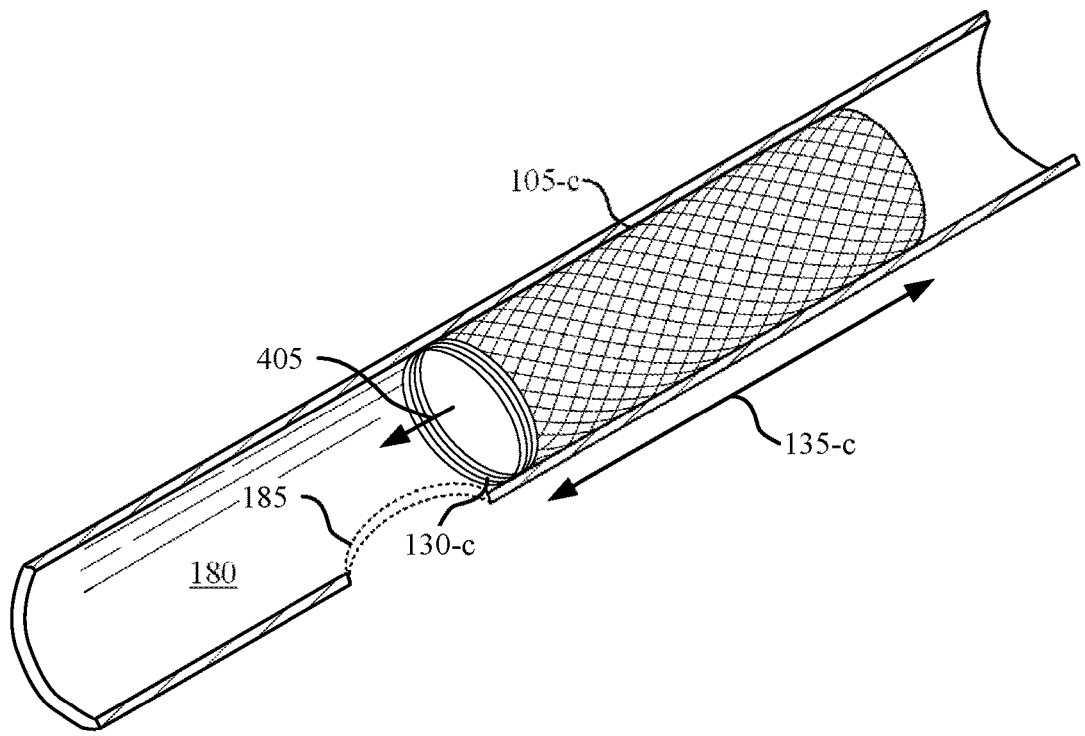
FIG. 4A illustrates a stent with a tubular deployable member in a stowed configuration in accordance with aspects of the present disclosure.

FIG. 4A shows a fully deployed stent 105-*c* within a body lumen 180 in accordance with aspects of the present disclosure. The stent 105-*c* may be an example of the stent 105 described with reference to FIGS. 1A-1C. The stent 105-*c* includes a deployable member 130-*c* that is shown in a stowed configuration. The deployable member 130-*c* is a tube configured to expand and collapse like an accordion, and is coupled with the end of the stent body 135-*c* proximate the access site 185. In the stowed configuration, the deployable member 130-*c* is collapsed down as shown in FIG. 4A and may be partially or fully housed within the stent body 135-*c*. The deployable member 130-*c* may deploy from the stent body 135-*c* by extending in length axially away from the stent body 135-*c* (as shown by arrow 405) until it is elongated (as shown in FIG. 4B), thereby increasing the body lumen contact surface area of the stent 105-*c*.

Figure 4B:
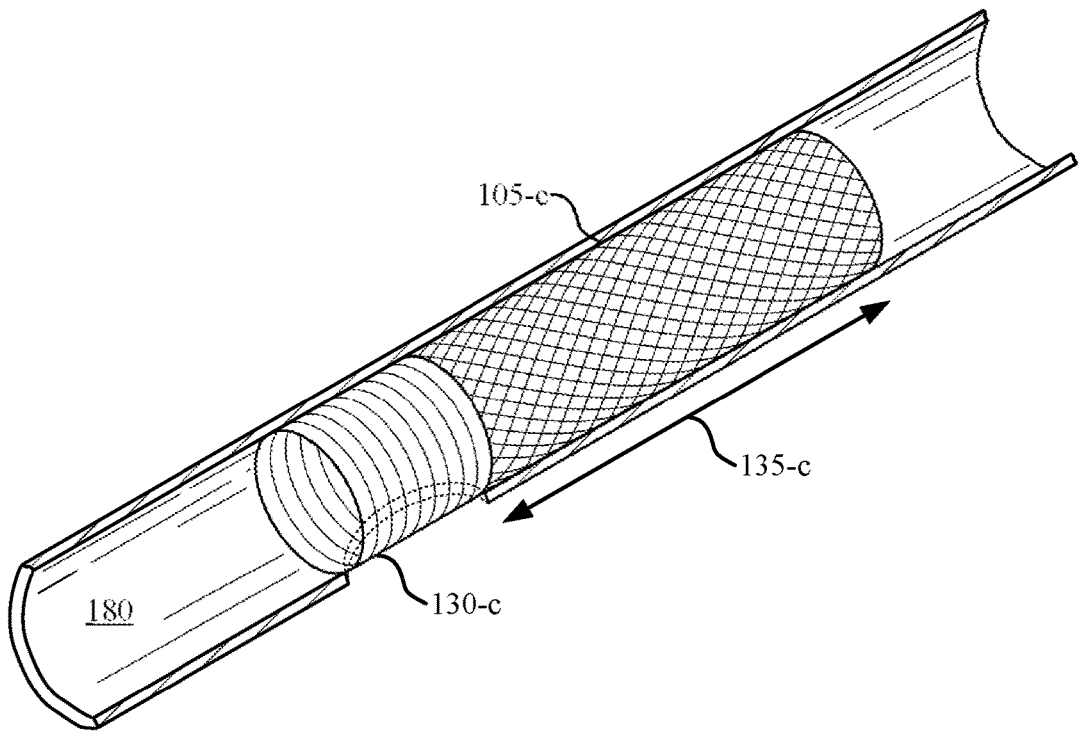
FIG. 4B illustrates a stent with a tubular deployable member in a deployed configuration in accordance with aspects of the present disclosure.

The deployable member 130-*c* may be configured to spring open to the deployed configuration shown in FIG. 4B when unconstrained. For example, the deployable member 130-*c* may be made from or include a material or component that stores elastic potential energy when in the stowed configuration. In such examples, some component of the stent delivery system 100 (e.g., the guidewire lumen 120 or the pusher 115) may hold the deployable member 130-*c* in the stowed configuration while the stent delivery system 100 is still within the body lumen 180. As such, once the particular component is withdrawn from the body lumen 180, the deployable member 130-*c* is free to spring open to the deployed configuration shown in FIG. 4B.

Additionally or alternatively, the deployable member 130-*c* may be detachably connected with some component of the stent delivery system 100 by a pull string (e.g., a surgical suture). In such examples, as the stent delivery system 100 is withdrawn from the body lumen 180, the deployable member 130-*c* is pulled into the deployed configuration shown in FIG. 4B by the stent delivery system 100 as it exits the access site 185. Once the stent delivery system 100 is fully withdrawn from the body lumen 180, the connection between the stent delivery system 100 and the deployable member 130-*c* may be detached (e.g., breaking or otherwise disconnecting the pull string).

The deployable member 130-*c* may include a frame or other support structure and may be made from the same material or materials as the stent body 135-*c*. In other examples, the deployable member 130-*c* is made from a different material than the stent body 135-*c*. The materials forming the structure of the deployable member 130-*c* may be densely arranged (e.g., mesh-like) so as to impede the flow of fluid through the deployable member 130-*c*. The deployable member 130-*c* may also include a web, coating, or some other covering (e.g., silicon, polyurethane, polytetrafluoroetheylene, fabric) that prevents or at least impedes the flow of fluid therethrough.

Figure 5A:
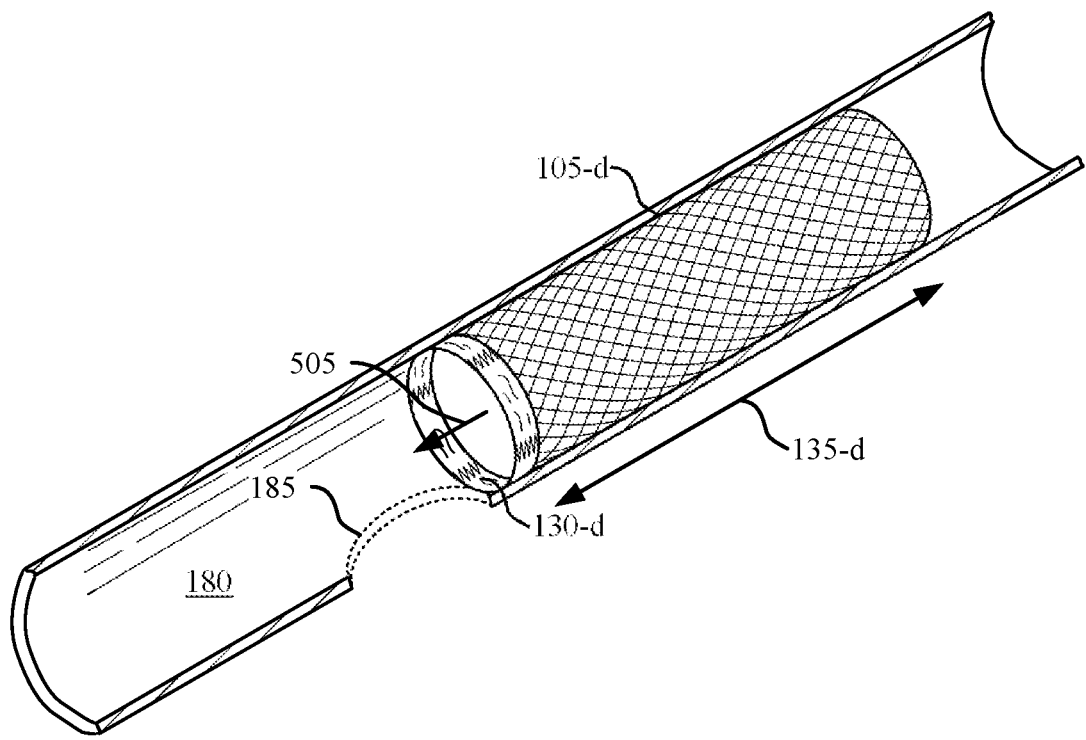
FIG. 5A illustrates a stent with a tubular deployable member in a stowed configuration in accordance with aspects of the present disclosure.

FIG. 5A shows a fully deployed stent 105-*d* within a body lumen 180 in accordance with aspects of the present disclosure. The stent 105-*d* may be an example of the stent 105 described with reference to FIGS. 1A-1C. The stent 105-*d* includes a deployable member 130-*d* that is shown in a stowed configuration. The deployable member 130-*d* is a tube configured to expand and collapse like an accordion, and is coupled with the end of the stent body 135-*d* proximate the access site 185. In the stowed configuration, the deployable member 130-*d* is collapsed down as shown in FIG. 5A and may be partially or fully housed within the stent body 135-*d*. The deployable member 130-*d* may deploy from the stent body 135-*d* by extending in length axially away from the stent body 135-*d*, as indicated by arrow 505, until it is elongated (as shown in FIG. 5B), thereby increasing the body lumen contact surface area of the stent 105-*d*.

Figure 5B:
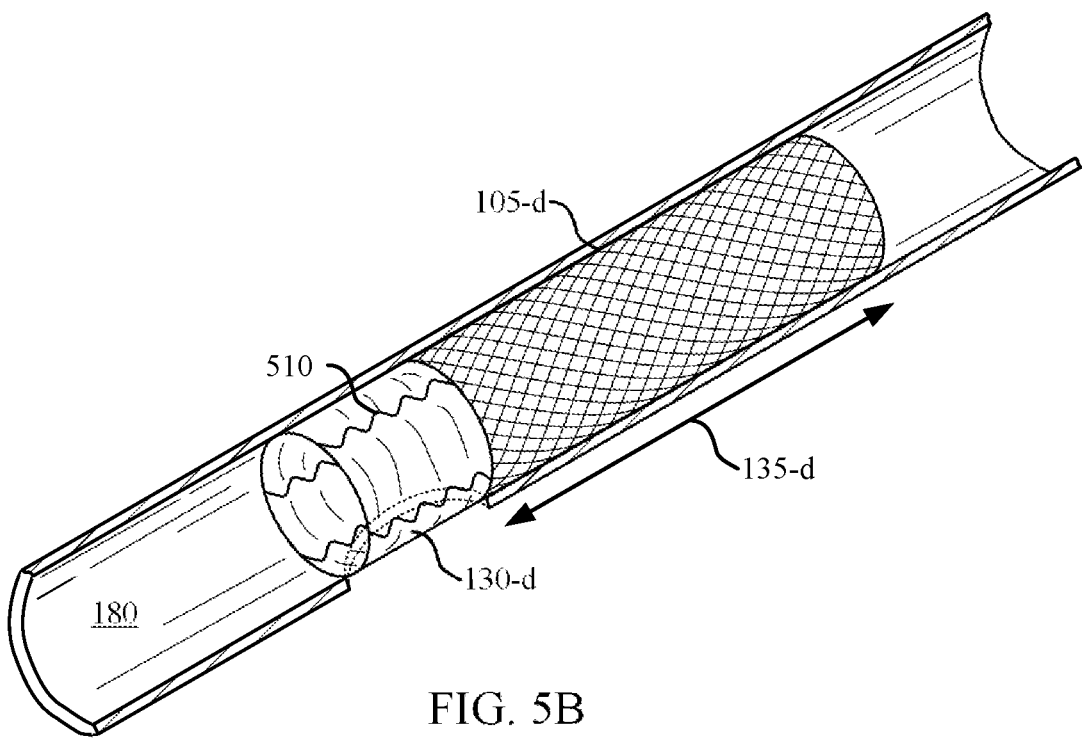
FIG. 5B illustrates a stent with a tubular deployable member in a deployed configuration in accordance with aspects of the present disclosure.

The deployable member 130-*d* may be configured to spring open to the deployed configuration shown in FIG. 5B when unconstrained. For example, the deployable member 130-*d* may be made from a material that stores elastic potential energy when in the stowed configuration. Addition or alternatively, the deployable member 130-*d* may include one or more integrated spring elements 510 that urge the deployable member 130-*d* to elongate axially. In such examples, some component of the stent delivery system 100 (e.g., the guidewire lumen 120 or the pusher 115) may hold the deployable member 130-*d* in the stowed configuration while the stent delivery system 100 is still within the body lumen 180. As such, once the particular component is withdrawn from the body lumen 180, the deployable member 130-*d* is free to spring open to the deployed configuration shown in FIG. 5B.

Additionally or alternatively, the deployable member 130-*d* may be detachably connected with some component of the stent delivery system 100 by a pull string (e.g., a surgical suture). In such examples, as the stent delivery system 100 is withdrawn from the body lumen 180, the deployable member 130-*d* is pulled into the deployed configuration shown in FIG. 5B by the stent delivery system 100 as it exits the access site 185. Once the stent delivery system 100 is fully withdrawn from the body lumen 180, the connection between the stent delivery system 100 and the deployable member 130-*d* may be detached (e.g., breaking or otherwise disconnecting the pull string).

The deployable member 130-*d* may include a frame or other support structure and may be made from the same material or materials as the stent body 135-*d*. In other examples, the deployable member 130-*d* is made from a different material than the stent body 135-*d*. The materials forming the structure of the deployable member 130-*d* may be densely arranged (e.g., mesh-like) so as to impede the flow of fluid through the deployable member 130-*d*. The deployable member 130-*d* may also include a web, coating, or some other covering (e.g., silicon, polyurethane, polytetrafluoroetheylene, fabric) that prevents or at least impedes the flow of fluid therethrough. Alternatively, the deployable member 130-*d* may be made from a relatively flimsy material that is held in a generally cylindrical shape by the integrated spring elements 510.

Figure 6A:
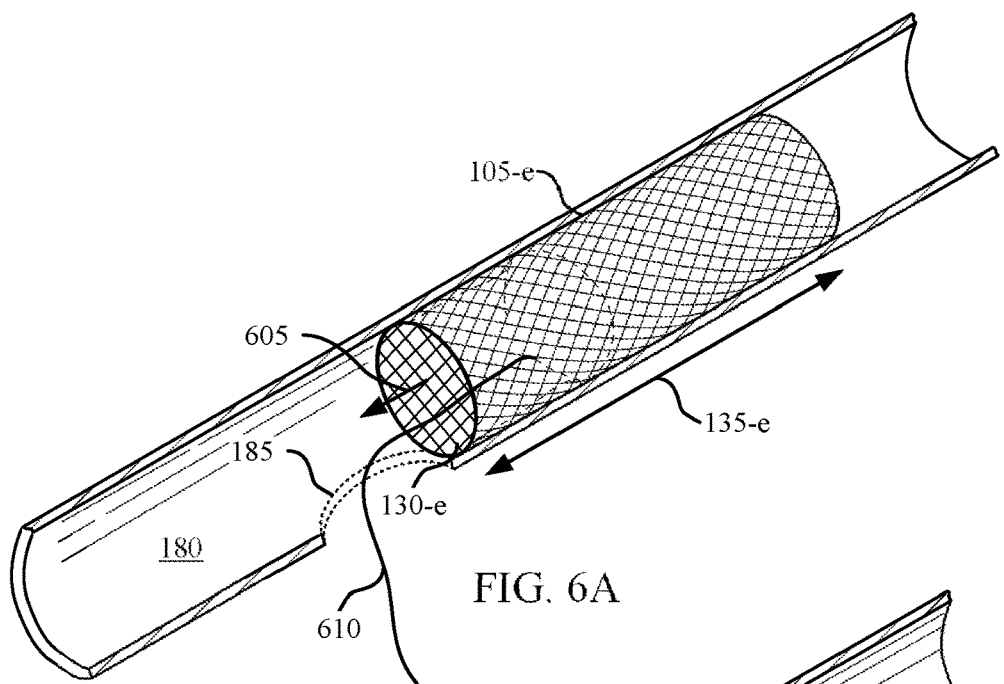
FIG. 6A illustrates a stent with a sleeve deployable member in a stowed configuration in accordance with aspects of the present disclosure.
Figure 6B:
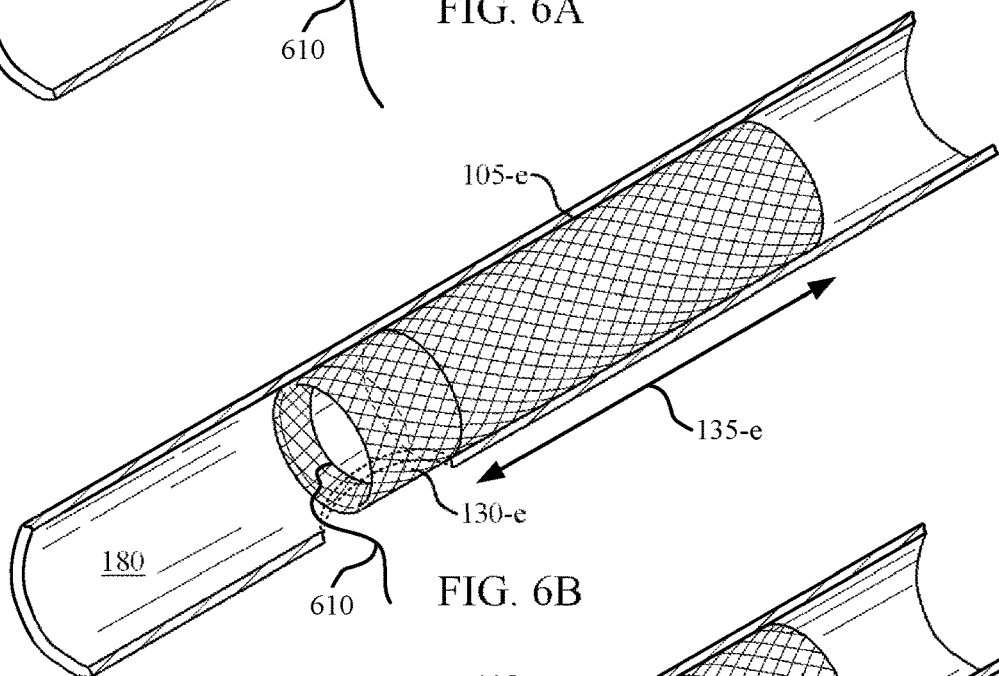
FIG. 6B illustrates a stent with a sleeve deployable member in a partially deployed configuration in accordance with aspects of the present disclosure.
Figure 6C:
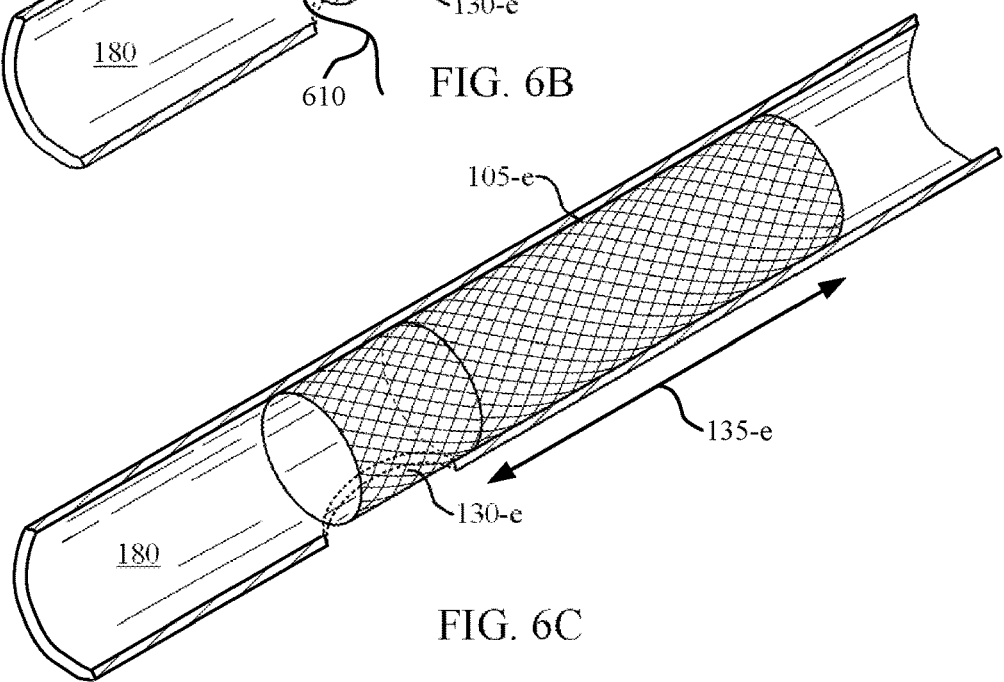
FIG. 6C illustrates a stent with a sleeve deployable member in a fully deployed configuration in accordance with aspects of the present disclosure.

FIG. 6A shows a fully deployed stent 105-*e* within a body lumen 180 in accordance with aspects of the present disclosure. The stent 105-*e* may be an example of the stent 105 described with reference to FIGS. 1A-1C. The stent 105-*e* includes a deployable member 130-*e* that is shown stowed within the stent body 135-*e*. The deployable member 130-*e* is a flexible sleeve. In the stowed configuration, the deployable member 130-*e* is folded inside the stent body 135-*e* as shown in FIG. 6A. The deployable member 130-*e* may deploy from the stent body 135-*e*, as indicated by arrow 605, by unrolling from inside the stent body 135-*e* (as shown in FIG. 6B) until it is fully unrolled (as shown in FIG. 6C), thereby increasing the body lumen contact surface area of the stent 105-*e*.

The deployable member 130-*e* is detachably connected with a pull string 610 or some other pull mechanism which is coupled with the stent delivery system 100. As the stent delivery system 100 is withdrawn from the body lumen 180, the deployable member 130-*e* is pulled by the pull string 610 until it unrolls from inside the stent body 135-*e* to outside the stent body 135-*e*, as shown in the progressions from FIG. 6A to FIG. 6C. Once the stent delivery system 100 is fully withdrawn from the body lumen 180, the pull string 610 may be detached from the deployable member 130-*e* or from the stent delivery system 100.

The deployable member 130-*e* may include a frame or other support structure and may be made from the same material or materials as the stent body 135-*e*. In other examples, the deployable member 130-*e* is made from a different material than the stent body 135-*e*. The materials forming the structure of the deployable member 130-*e* may be densely arranged (e.g., mesh-like) so as to impede the flow of fluid through the deployable member 130-*e*. The deployable member 130-*e* may also include a web, coating, or some other covering (e.g., silicon, polyurethane, polytetrafluoroetheylene, fabric) that prevents or at least impedes the flow of fluid therethrough.

Figure 7A:
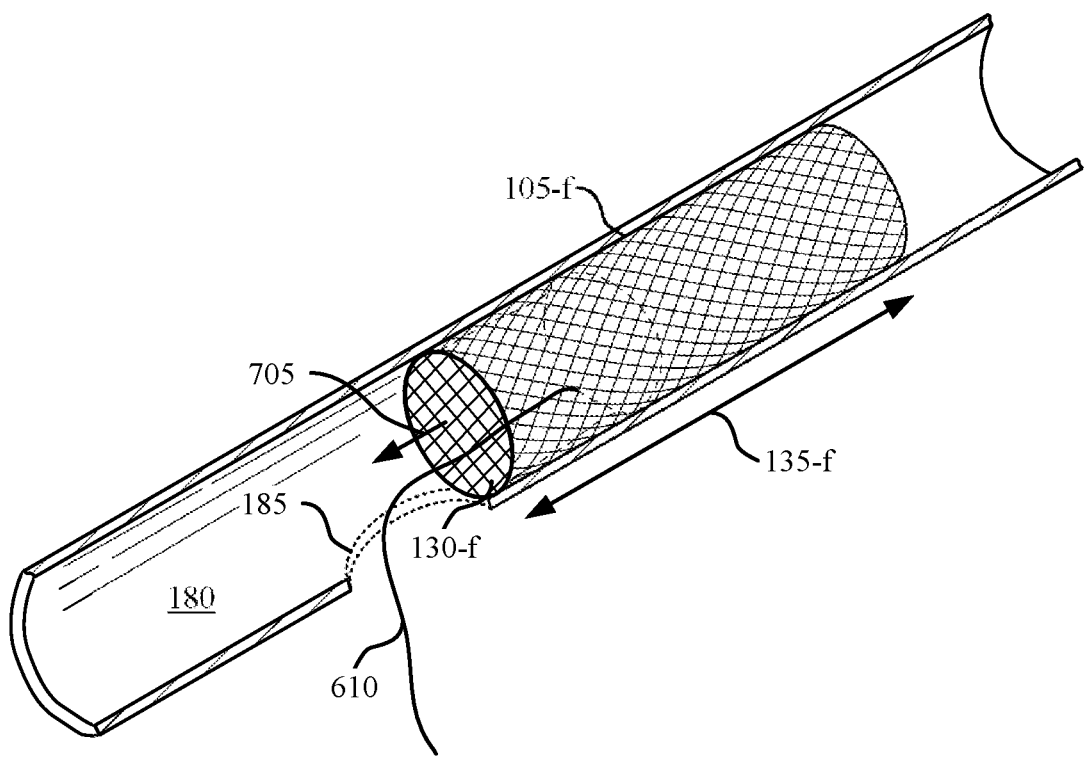
FIG. 7A illustrates a stent with a tubular deployable member in a stowed configuration in accordance with aspects of the present disclosure.
Figure 7B:
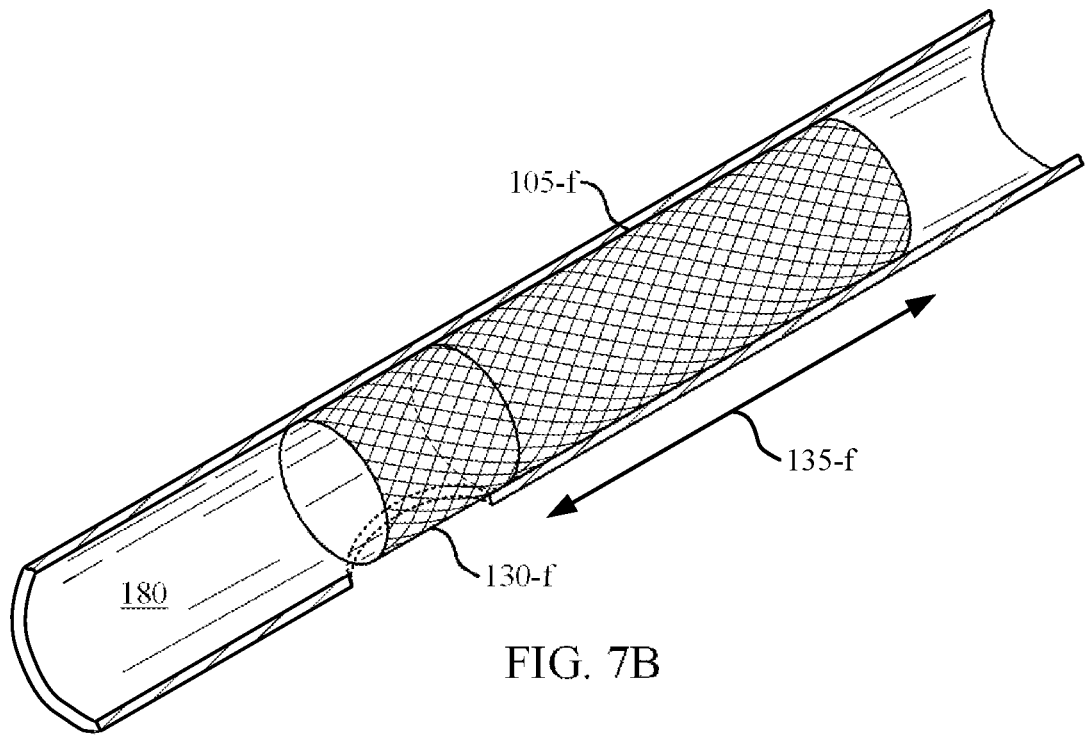
FIG. 7B illustrates a stent with a tubular deployable member in a deployed configuration in accordance with aspects of the present disclosure.
Figure 8:
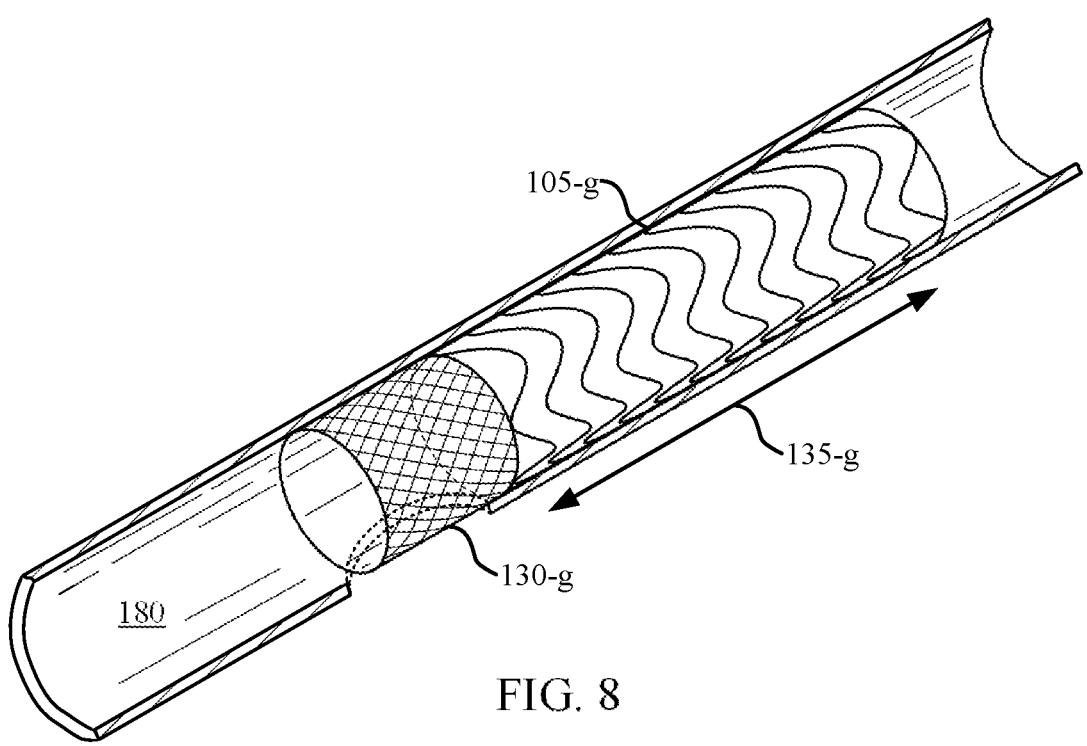
FIG. 8 illustrates a stent with a tubular deployable member in a deployed configuration in accordance with aspects of the present disclosure.

FIG. 7A shows a fully deployed stent 105-*f* within a body lumen 180 in accordance with aspects of the present disclosure. The stent 105-*f* may be an example of the stent 105 described with reference to FIGS. 1A-1C. The stent 105-*f* includes a deployable member 130-*f* that is shown stowed within the stent body 135-*f*. The deployable member 130-*f* is a tubular member sized to fit inside the stent body 135-*f*. In some examples, the deployable member 130-*f* is similar in structure and materials as the stent body 135-*f*, except with a smaller diameter. In the stowed configuration, the deployable member 130-*f* is housed inside the stent body 135-*f* as shown in FIG. 7A. The distal end of the deployable member 130-*f* is attached to the proximal end of the stent body 135-*f* by a flexible cuff or sleeve. The deployable member 130-*e* may deploy from the stent body 135-*f*, as indicated by arrow 705, by translating coaxially with the stent body 135-*f* from inside the stent body 135-*f* (as shown in FIG. 6A) to outside the stent body 135-*f* (as shown in FIG. 7B), thereby increasing the body lumen contact surface area of the stent 105-*f*.

The deployable member 130-*f* is detachably connected with a pull string 610 which is coupled with the stent delivery system 100. As the stent delivery system 100 is withdrawn from the body lumen 180, the deployable member 130-*f* is pulled by the pull string 610 until it exits from inside the stent body 135-*f* to outside the stent body 135-*f*. Once the stent delivery system 100 is fully withdrawn from the body lumen 180, the pull string 610 may be detached from the deployable member 130-*f* or from the stent delivery system 100.

The deployable member 130-*f* may include a frame or other support structure and may be made from the same material or materials as the stent body 135-*f*. In other examples, the deployable member 130-*f* is made from a different material than the stent body 135-*f*. The materials forming the structure of the deployable member 130-*f* may be densely arranged (e.g., mesh-like) so as to impede the flow of fluid through the deployable member 130-*f*. The deployable member 130-*f* may also include a web, coating, or some other covering (e.g., silicon, polyurethane, polytetrafluoroetheylene, fabric) that prevents or at least impedes the flow of fluid therethrough.

FIG. 8 shows a fully deployed stent 105-*g* within a body lumen 180 in accordance with aspects of the present disclosure. The stent 105-*g* may be an example of the stent 105 described with reference to FIGS. 1A-1C. Unlike the stent bodies depicted in the previous figures, the stent body 135-*g* is made from a helically wrapped wire-form construction.

Although not depicted, the stent body 135-g may instead be made from a laser-cut construction. In any case, the deployable member 130-g is made from a different construction, such as a braided stent construction. The wire-form or laser-cut stent body 135-g experiences less foreshortening when deployed from the stent delivery system 100 than a braided stent. As such, the stent body 135-g may be more accurately placed within the body lumen 180 across the target site (e.g., across the major duodenal papilla). The deployable member 130-g may be an example of or include features of any of the deployable members 135-c, 135-d, 135-e, or 135-f described with reference to FIGS. 4-7.

Figure 9:
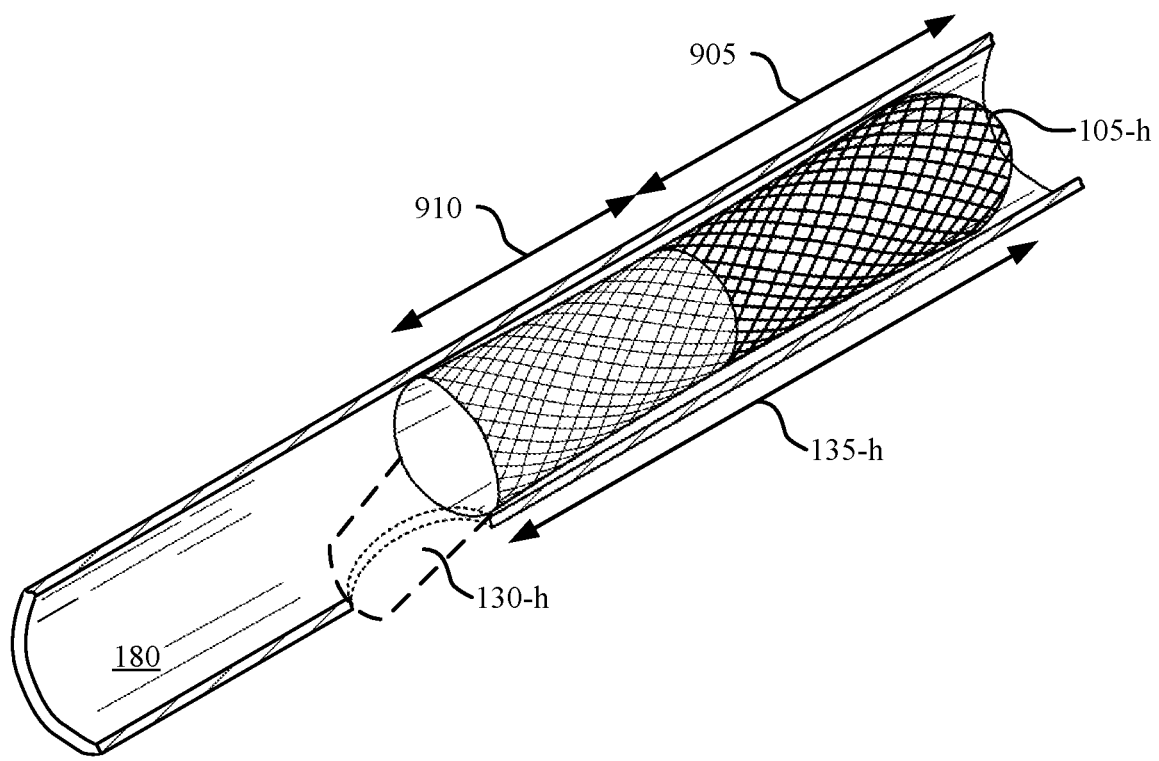
FIG. 9 illustrates a stent with a variable radial compression profile in accordance with aspects of the present disclosure.

FIG. 9 shows a fully deployed stent 105-h within a body lumen 180 in accordance with aspects of the present disclosure. The stent 105-h includes a stent body 135-h and a deployable member 130-h. The stent 105-h and the deployable member 130-h may be an example of or include features of any of the stents 105 or deployable members 130 described with reference to FIGS. 1-8. The stent 105-h may be configured to create a variable radial force profile across the length of the stent body 135-h. For example, the radial compression exerted by the stent 105-h on the inner surface of the body lumen 180 may be greater at the distal end of the stent 105-h (with respect to the access site 185) than at the proximal end. In some cases, the radial force is greater along a distal section 905 of the stent body 135-h than along a proximal section 910. A variable radial compression profile may improve stent migration resistance, long term stent patency, and reduce tumor in-growth.

In some examples, the radial force profile is created by forming the distal portion 905 of the stent body 135-h with braided wires that are thicker than those along the proximal portion 910 (as illustrated by the darker lines in distal section 905). As such, the thicker wires will be stiffer and therefore capable of exerting a greater expansion force. For example, the wires in the proximal portion 910 may have a diameter in the range of 0.006 inches to 0.008 inches while the wires along the distal portion 905 may have a diameter in the range of 0.0075 inches to 0.010 inches. Instead of using thicker wires, the distal section 905 may be made from a different material that is stiffer than the material used for the proximal section 910. In other embodiments, the variable radial force is accomplished by forming the distal portion 905 with a wire-form or laser-cut construction, whereas the proximal portion 910 of the stent body 135-h is formed of a braided construction. Although two sections 905, 910 of varying radial expansion force are illustrated, it may be appreciated that more sections may be included to create a more linearly increasing force profile.

Figure 10:
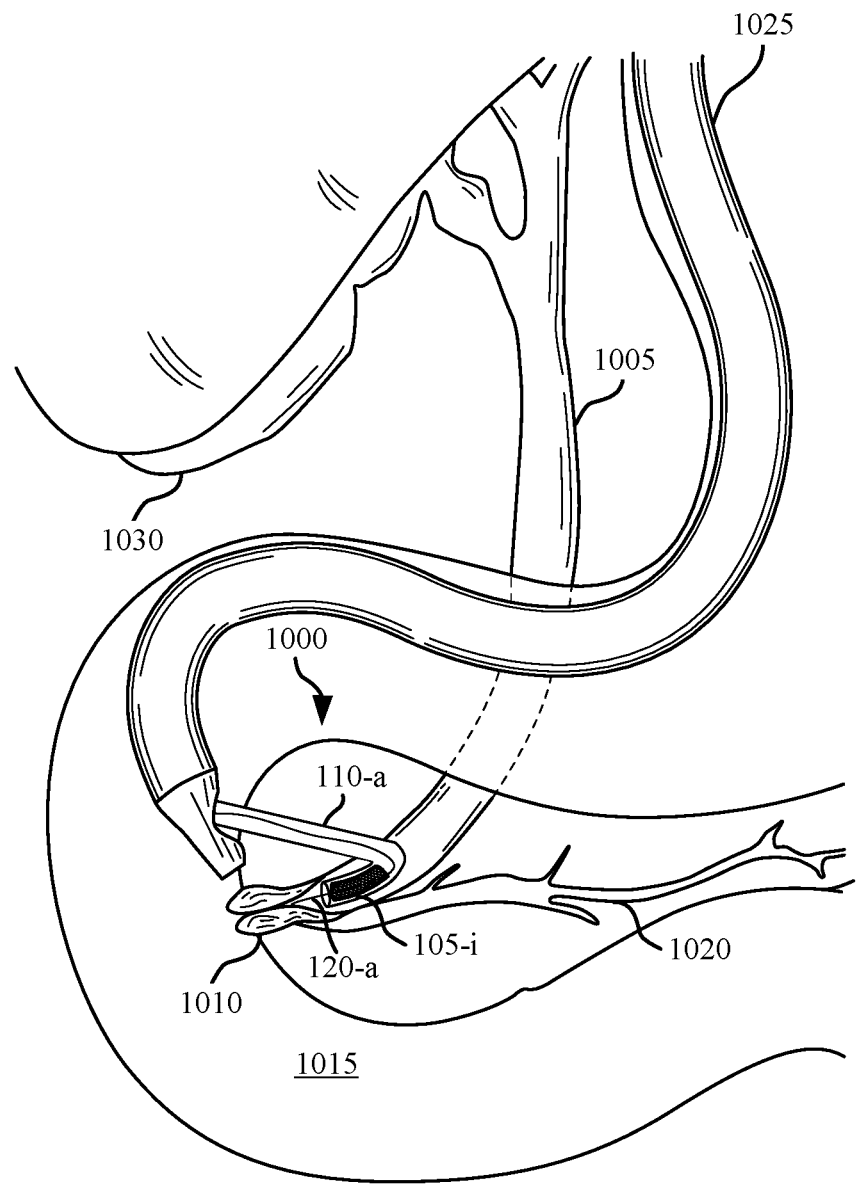
FIG. 10 illustrates a stent delivery system for delivering a stent to a body lumen of the pancreaticobiliary system in accordance with aspects of the present disclosure.

Embodiments of the present disclosure are now described in the context of a particular stenting procedure referred to as an Endoscopic Ultrasound Guided Biliary Drainage (EUS-BD) procedure. With reference to FIG. 10, a stent delivery system 1000 for placing a stent 105-i within a body lumen within the pancreaticobiliary system is illustrated in accordance with aspects of the present disclosure. The stent delivery system 1000 may be an example of the stent delivery system 100 described with reference to FIGS. 1A-1C, and the stent 105-i may be an example of or include features of any stent 105 described with reference to FIGS. 1-9. The illustrated portions of the pancreaticobiliary system include the common bile duct 1005, which drains bile from the gallbladder 1030 into the duodenum 1015, where the bile mixes and reacts with digesting food. As shown, the common bile duct 1005 joins with the pancreatic duct 1020 at the major duodenal papilla 1010 (shown obstructed) before draining into the duodenum 1015.

The drainage procedure generally includes a clinician advancing an endoscope 1025 (e.g., an EUS endoscope) into the lumen of a patient's duodenum 1015 to a position in which the bile ducts may be visualized (e.g., via endosonography). As described with reference to FIG. 1A, the clinician may then access the common bile duct 1005 by advancing a needle or a cannula (not shown) from a working channel of the endoscope 1025, through the wall of the duodenum 1015 (i.e., trans-duodenally), and then through the wall of the common bile duct 1005, thereby creating an access site 185. The clinician may then advance a guidewire lumen 120-a through the access site 185, and then advance an outer sheath 110-a of the stent delivery system 1000 over the guidewire lumen 120-a and into the common bile duct 1005, thereby dilating the access site 185, as described with reference to FIG. 1B.

Figure 11:
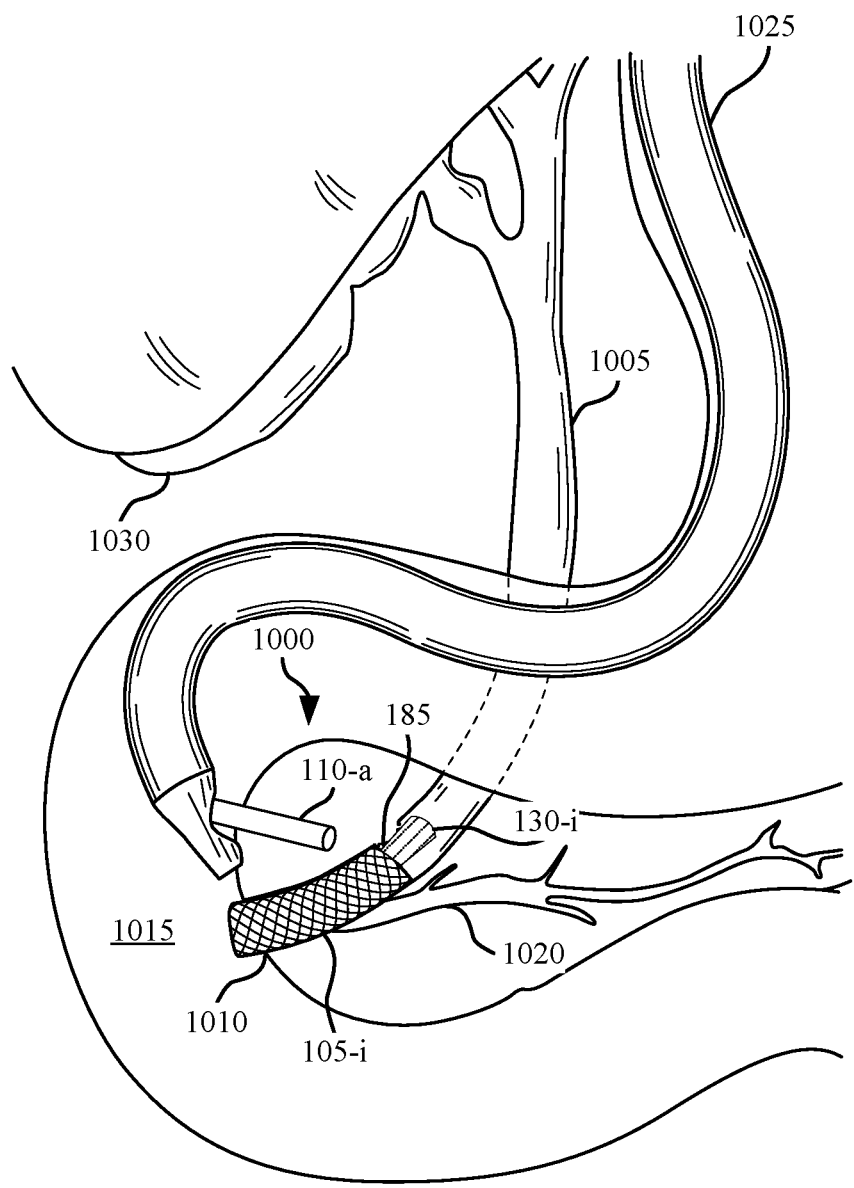
FIG. 11 illustrates a stent delivery system for delivering a stent to a body lumen of the pancreaticobiliary system in accordance with aspects of the present disclosure.

With reference to FIG. 11, once the stent delivery system 1000 is in place, the stent 105-i may deployed from the stent delivery system 1000 across the major duodenal papilla 1010 to restore normal flow through the common bile duct 1005. As described with reference to FIG. 1C, once the stent delivery system 1000 is withdrawn from the common bile duct 1005, the deployable member 130-i may deploy from the body of stent 105-i to cover the access site 185. The deployable member 130-i may be an example of or include features of any deployable member 130 described with reference to FIGS. 1-9.

Figure 12A:
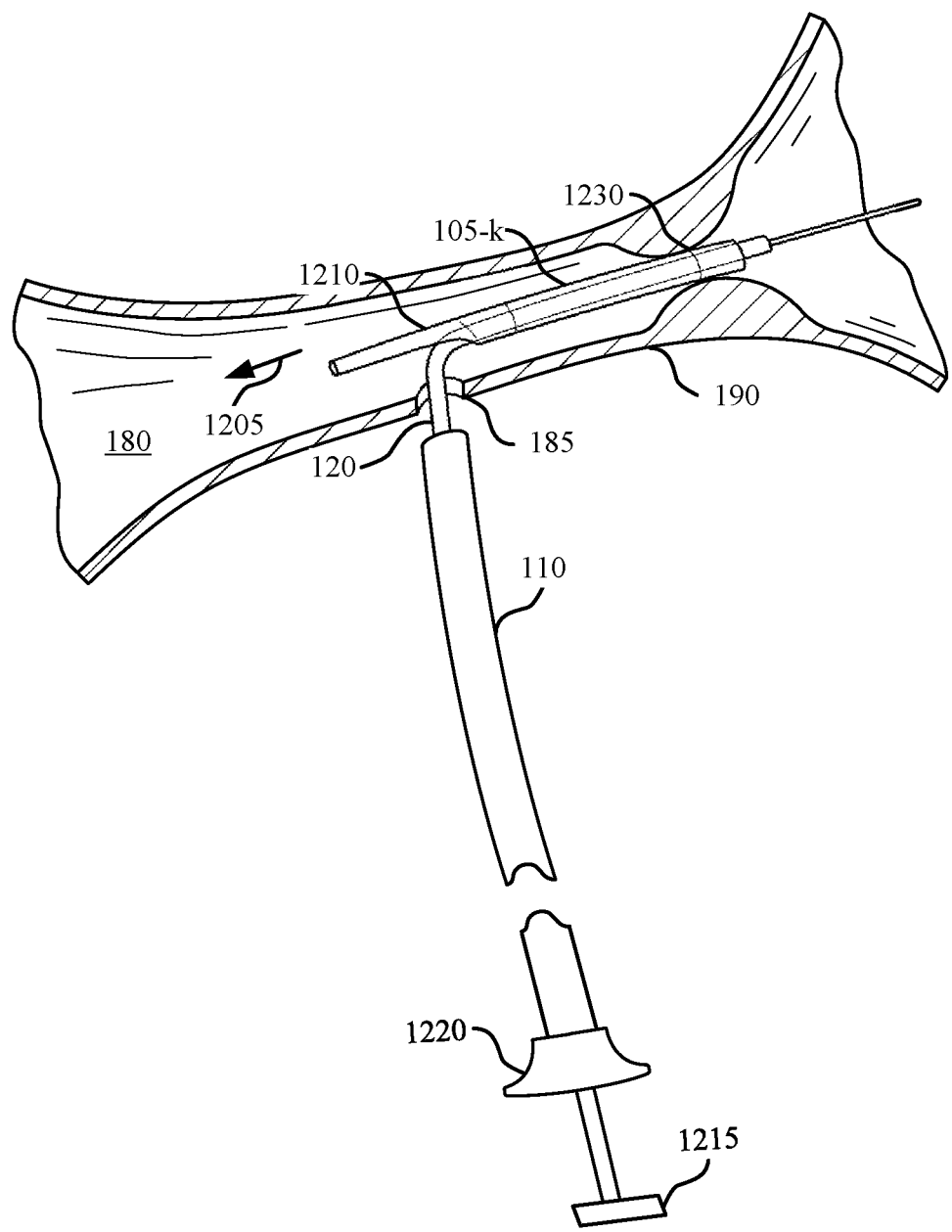
FIG. 12A illustrates a stent delivery system with the stent retracted towards the access site in accordance with aspects of the present disclosure.

FIG. 12A illustrates a stent delivery system 1200-a with the stent 105-k retracted towards the access site 185 in accordance with aspects of the present disclosure. Once the outer sheath 110 is removed through the access site 185, the stent 105-k may be pulled towards the access site 185 in a proximal direction, as indicated by arrow 1205. For example, the stent 105-k may be pulled toward the access site 185 until the proximal portion 1210 of the stent 105-k at least partially covers the access site 185. The stent 105-k may be retracted towards the access site 185 by pulling the guidewire lumen 120 in a proximal direction. For example, the stent 105-k may be pulled towards the access site 185 by pulling the hub 1215 of the guidewire lumen 120 in a proximal direction. In some cases, the stent 105-k may be pulled towards the access site 185 by pulling the hub 1215 of the guidewire lumen 120, the lumen member (not shown), and the outer sheath hub 1220 of the outer sheath 110.

Furthermore, the stent 105-k may be repositioned within the body lumen 180 to at least partially cover the access site 185. To deploy the stent 105-k within the body lumen 180, a primary constrainment member 1230 may be released. The stent 105-k may be deployed by pulling the primary constrainment member 1230 in a proximal direction, pulling one or more tethers coupled with the primary constrainment member 1230, or both. In some cases, the stent 105-k may be disposed onto the guidewire lumen 120 such that the guidewire lumen 120 is inside the stent 105-k along a distal portion of the stent 105-k and outside of the stent 105-k along the proximal portion 1210 of the stent 105-k. This configuration may be referred to a partial side-saddle configuration.

Figure 12B:
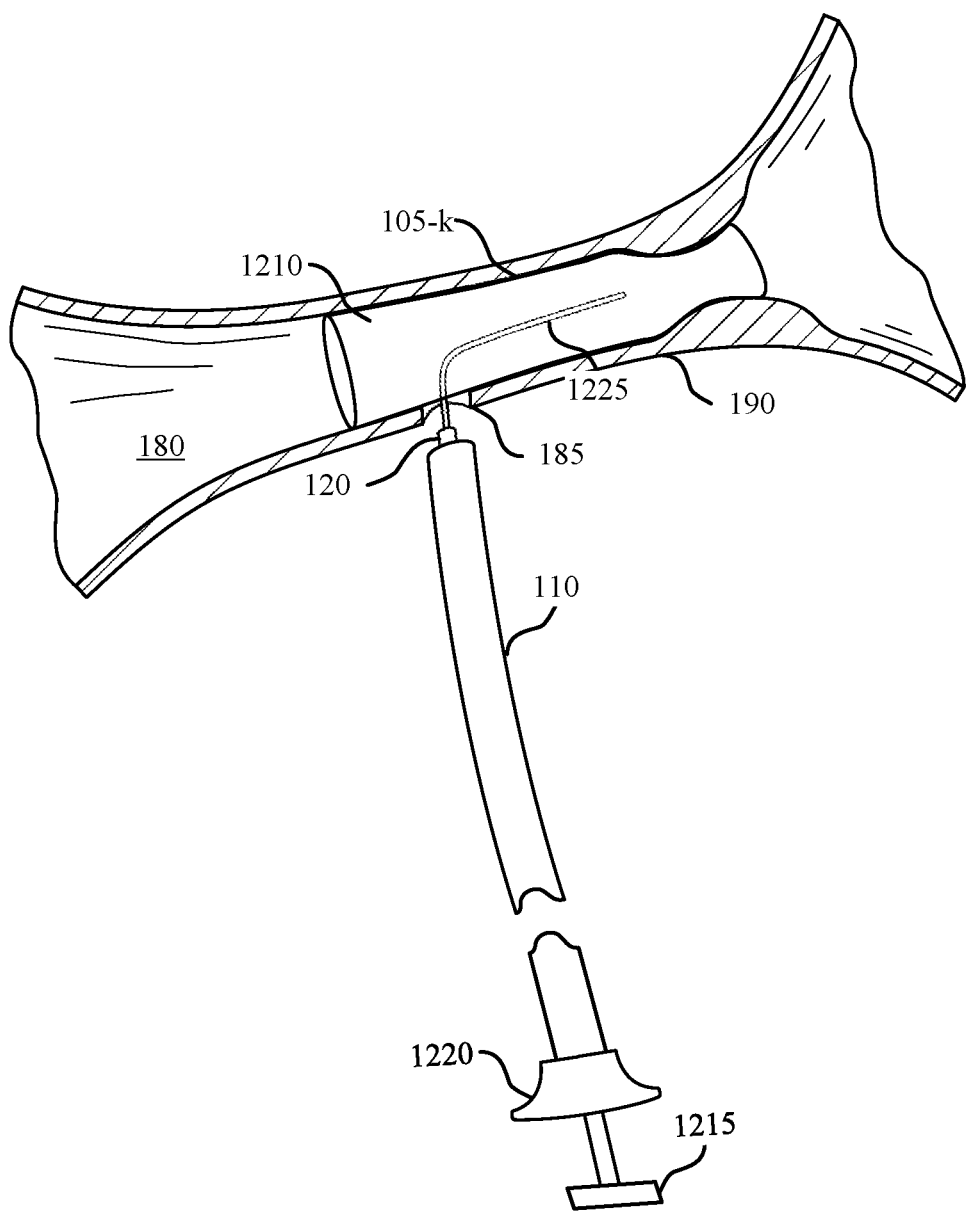
FIG. 12B illustrates a stent delivery system with the stent fully deployed in accordance with aspects of the present disclosure.

FIG. 12B illustrates a stent delivery system 1200-b with the stent 105-k fully deployed in accordance with aspects of the present disclosure. In the case of a self-expanding stent, the stent 105-k expands to contact the inner surface of the body lumen 180. Once the stent 105-k expands within the body lumen 180, the guidewire lumen 120 and the guidewire 1225 are withdrawn through the access site 185. In some cases, the guidewire lumen 120 and the guidewire 1225 may extend through a hole in a wall of the stent 105-k. In such cases, the guidewire lumen 120 and the guidewire 1225 may be withdrawn through the hole in the wall of the stent 105-*k*.

In some cases, the hole in the wall of the stent may allow for fluid from the body lumen 180 to leak out into the surrounding tissue and organs. For example, because the stent 105-*k* may be in the partial side-saddle configuration, the hole in the stent 105-*k* may align with the access site 185. In such cases, and as described below in further detail, the system 1200-*b* may include a coverage member. The coverage member may be configured to at least partially cover the hole in the wall of the stent 105-*k* upon withdrawing the guidewire lumen 120 through the hole in the wall of the stent 105-*k*, thereby at least partially sealing the access site 185 and preventing the leakage of fluid from the body lumen 180.

Figure 13:
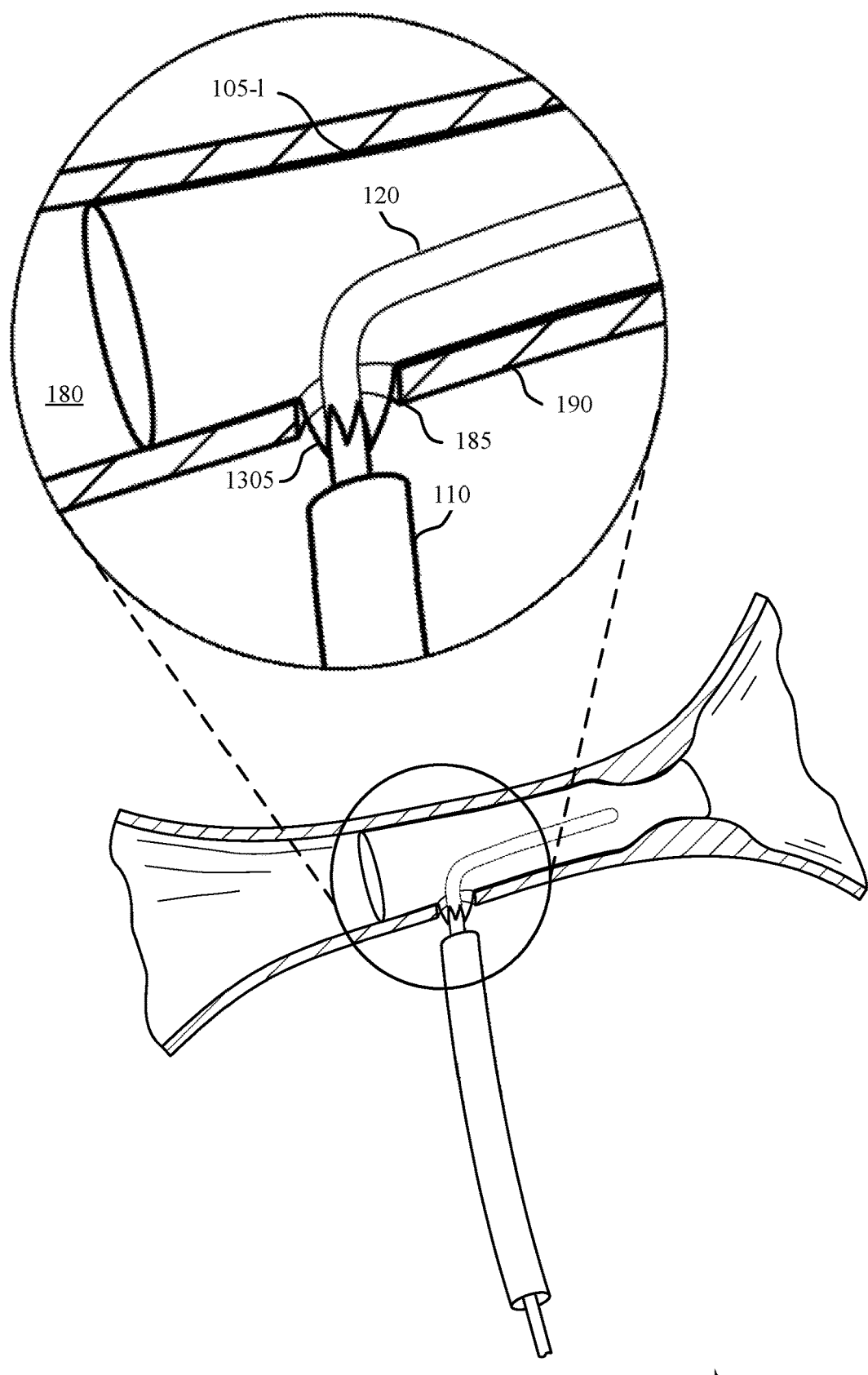
FIG. 13 illustrates a stent delivery system with a stent with a flap valve in accordance with aspects of the present disclosure.

FIG. 13 illustrates a stent delivery system 1300 with a stent 105-1 with a flap valve in accordance with aspects of the present disclosure. Once the guidewire lumen 120 and the guidewire are withdrawn through the hole in the wall of the stent 105-1, the coverage member 1305 may at least partially cover the hole in the wall of the stent 105-1. For example, the coverage member 1305 may be an example of a flap valve. The flap valve may be configured to seal the hole in the wall of the stent 105-1 when the guidewire lumen 120 is withdrawn through the hole in the wall of the stent 105-1. For example, the flap valve may be a one-way control valve. The flap valve may be positioned on an inner diameter of the stent 105-1. In some cases, the flap valve may include one or more flaps spaced around a circumference of the hole in the wall of the stent 105-1 such that the one or more flaps may align to form a closed flap valve.

Figure 14:
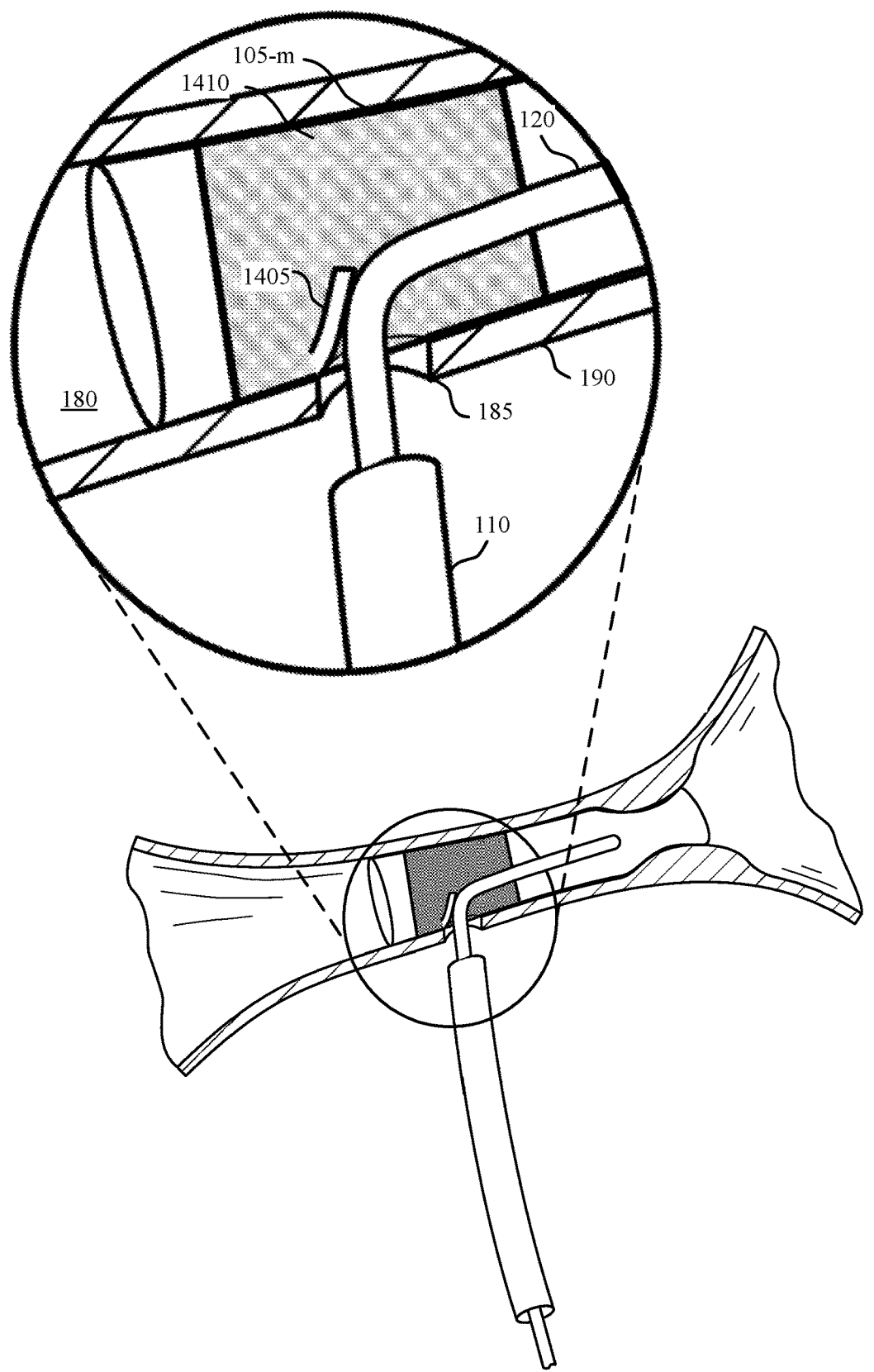
FIG. 14 illustrates a stent delivery system with a stent with a hinged valve in accordance with aspects of the present disclosure.

FIG. 14 illustrates a stent delivery system 1400 with a stent 105-*m* with a hinged valve in accordance with aspects of the present disclosure. Once the guidewire lumen 120 and the guidewire are withdrawn through the hole in the wall of the stent 105-*m*, the coverage member 1405 may at least partially cover the hole in the wall of the stent 105-*m*. For example, the coverage member 1405 may be an example of a hinged valve. The hinged valve may be configured to hinge such that when the guidewire lumen 120 is withdrawn through the hole in the wall of the stent 105-*m*, the hole in the wall of the stent 105-*m* may be covered.

In some examples, the hinged valve may rotate on an axis to remain open when the guidewire lumen 120 is positioned through the hole in the wall of the stent 105-*m* and closed when the guidewire lumen 120 is withdrawn through the hole in the wall of the stent 105-*m*. In some cases, the hinged valve may be spring-loaded such that the hinged valve recoils when the guidewire lumen 120 is withdrawn through the hole. For example, the hinged valve may be made from or include a material or component that stores elastic potential energy when the guidewire lumen 120 is positioned through the hole in the wall of the stent 105-*m*. In some cases, the stent delivery system 1400 may include a polymer jacket 1410 disposed on the outer surface of a central portion of the stent 105-*m*. In such cases, the hinged valve may be coupled to the polymer jacket 1410.

Figure 15:
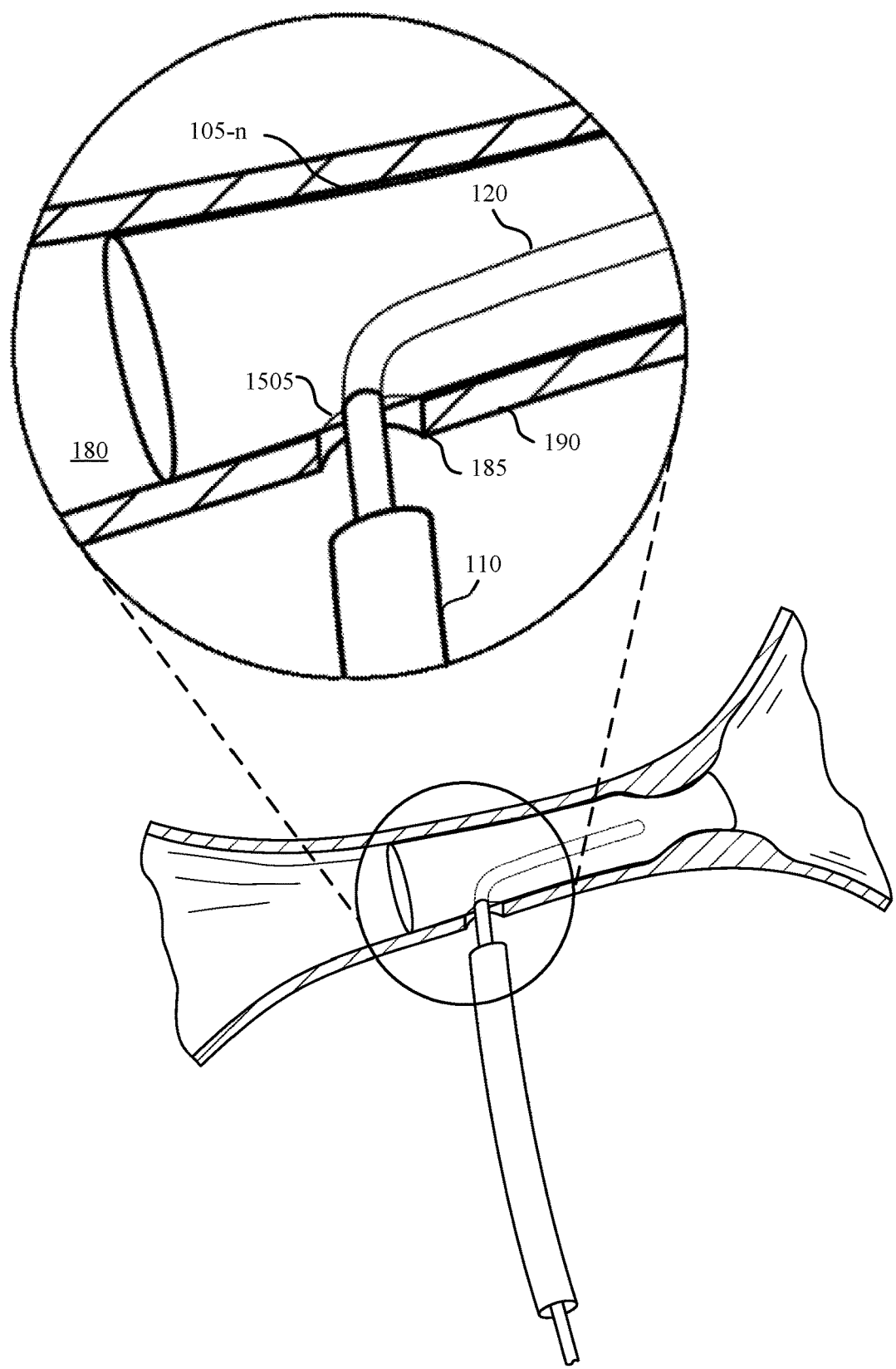
FIG. 15 illustrates a stent delivery system with a stent with a self-sealing membrane in accordance with aspects of the present disclosure.

FIG. 15 illustrates a stent delivery system 1500 with a stent 105-*n* with a self-sealing membrane in accordance with aspects of the present disclosure. Once the guidewire lumen 120 and the guidewire are withdrawn through the hole in the wall of the stent 105-*n*, the coverage member 1505 may at least partially cover the hole in the wall of the stent 105-*n*. For example, the coverage member 1505 may be an example of a self-sealing membrane material disposed on an outer surface of the wall of the stent 105-*n*. The self-sealing membrane material may be configured to seal the hole in the wall of the stent 105-*n* when the guidewire lumen 120 is withdrawn through the hole in the wall of the stent 105-*n*. For example, the self-sealing membrane material may include a pin hole that closes to a diameter to prevent bile leakage.

Figure 16:
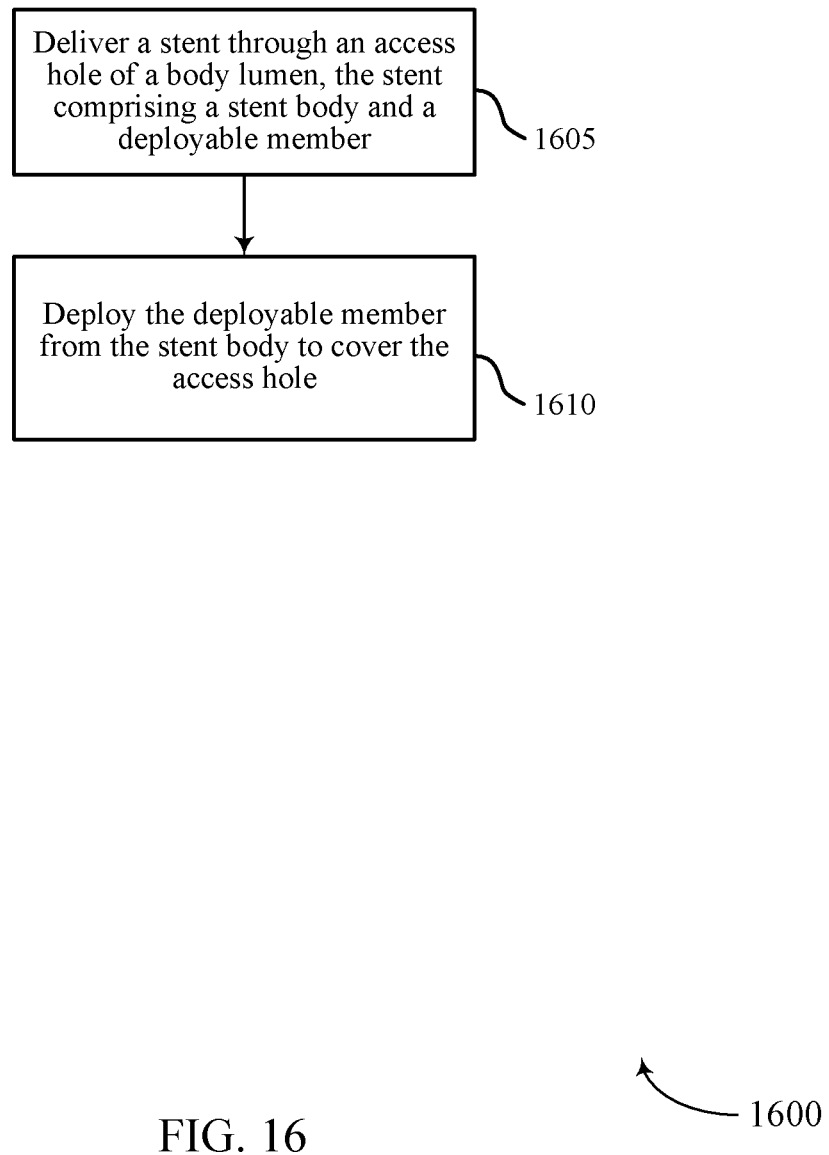
FIGS. 16-18 illustrate flowcharts of a method for delivering a stent within a body lumen in accordance with aspects of the present disclosure.

FIG. 16 shows a flowchart illustrating a method 1600 for stenting a body lumen 180 in accordance with various aspects of the present disclosure. The steps of method 1600 may be performed with any of the systems or components described with reference to FIGS. 1-11 and may be an example of aspects of the particular procedure described with reference to FIGS. 10-11. At block 1605, the method 1600 may include delivering a stent 105 through an access site 185 of a body lumen 180. As described with reference to FIGS. 1-9, the stent 105 may comprise a stent body 135 and a deployable member 130. At block 1610, the method 1600 may further include deploying the deployable member 130 from the stent body 135 to cover the access site 185.

Figure 17:
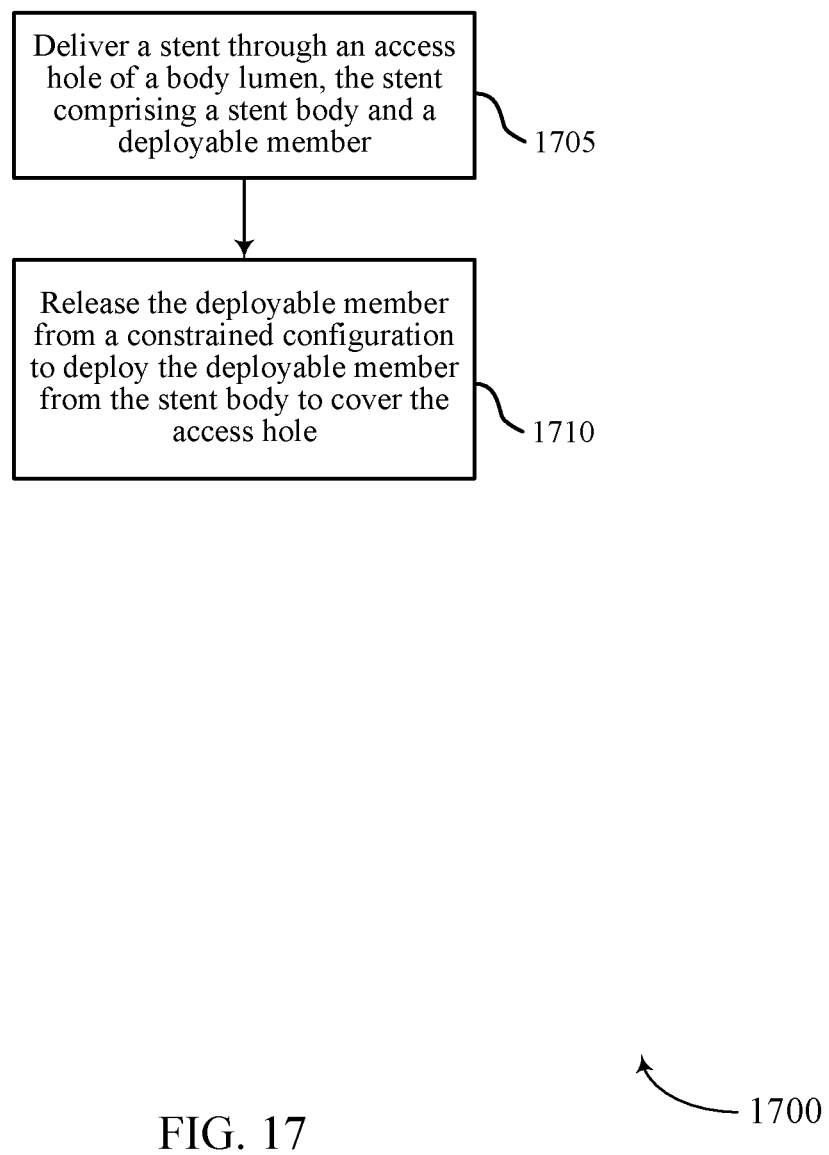

FIG. 17 shows a flowchart illustrating a method 1700 for stenting a body lumen 180 in accordance with various aspects of the present disclosure. The steps of method 1700 may be performed with any of the systems or components described with reference to FIGS. 1-11 and may be an example of aspects of the particular procedure described with reference to FIGS. 10-11. At block 1705, the method 1700 may include delivering a stent 105 through an access site 185 of a body lumen 180. As described with reference to FIGS. 1-9, the stent 105 may comprise a stent body 135 and a deployable member 130. At block 1710, the method 1300 may further include releasing the deployable member 130 from a constrained configuration to deploy the deployable member 130 from the stent body 135 to cover the access site 185.

Figure 18:
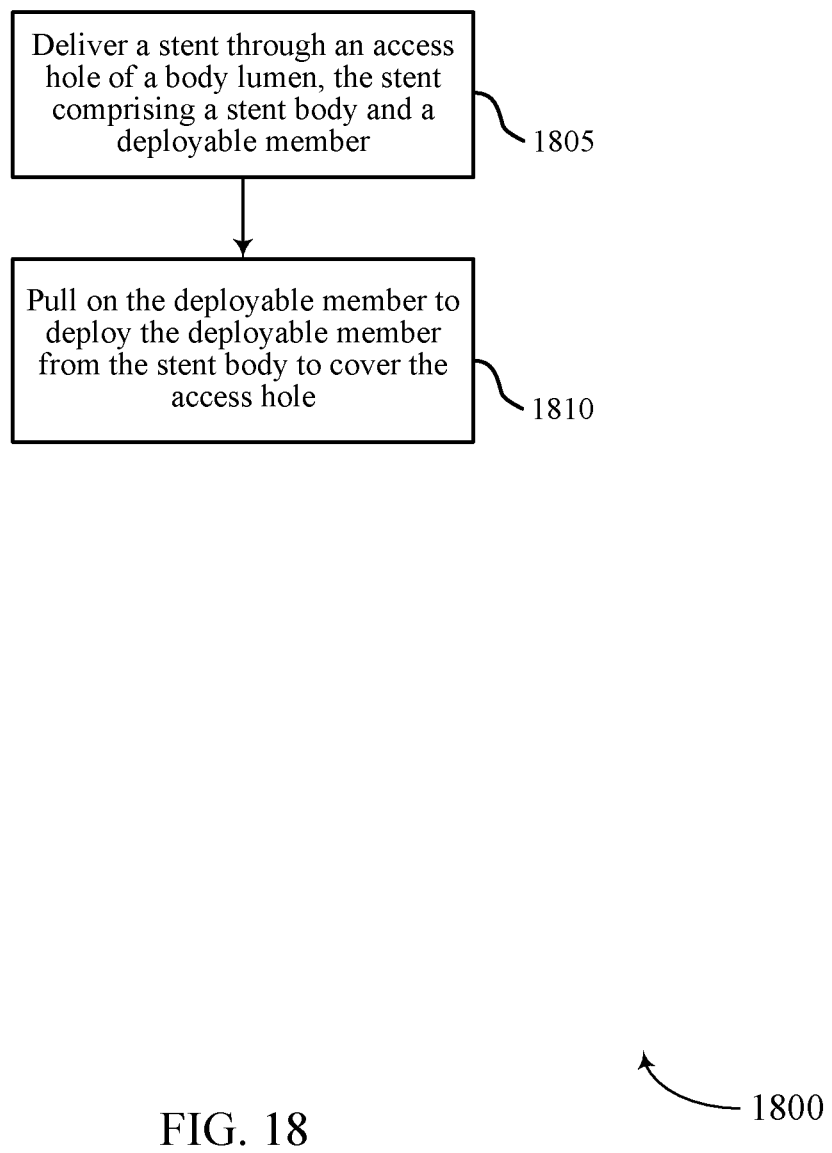

FIG. 18 shows a flowchart illustrating a method 1800 for stenting a body lumen 180 in accordance with various aspects of the present disclosure. The steps of method 1400 may be performed with any of the systems or components described with reference to FIGS. 1-11 and may be an example of aspects of the particular procedure described with reference to FIGS. 10-11. At block 1805, the method 1800 may include delivering a stent 105 through an access site 185 of a body lumen 180. As described with reference to FIGS. 1-9, the stent 105 may comprise a stent body 135 and a deployable member 130. At block 1810, the method 1800 may further include pulling on the deployable member 130 to deploy the deployable member 130 from the stent body 135 to cover the access site 185.

It should be noted that these methods describe possible implementation, and that the operations and the steps may be rearranged or otherwise modified such that other implementations are possible. In some examples, aspects from two or more of the methods may be combined. For example, aspects of each of the methods may include steps or aspects of the other methods, or other steps or techniques described herein.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed herein.

While several embodiments of the present disclosure have been described and illustrated herein, those of ordinary skill in the art will readily envision a variety of other means or structures for performing the functions or obtaining the results or one or more of the advantages described herein, and each of such variations or modifications is deemed to be within the scope of the present disclosure. More generally, those skilled in the art will readily appreciate that all parameters, dimensions, materials, and configurations described herein are meant to be exemplary and that the actual parameters, dimensions, materials, or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, or method described herein. In addition, any combination of two or more such features, systems, articles, materials, kits, or methods, if such features, systems, articles, materials, kits, or methods are not mutually inconsistent, is included within the scope of the present disclosure.

All definitions, as defined and used herein, should be understood to control over dictionary definitions, definitions in documents incorporated by reference, or ordinary meanings of the defined terms.

The indefinite articles "a" and "an," as used herein in the specification and in the claims, unless clearly indicated to the contrary, should be understood to mean "at least one." Also, as used herein, including in the claims, "or" as used in a list of items (for example, a list of items prefaced by a phrase such as "at least one of" or "one or more") indicates an inclusive list such that, for example, a list of at least one of A, B, or C means A or B or C or AB or AC or BC or ABC (i.e., A and B and C).

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

What is claimed is:

1. A stent comprising:
   a stent body; and
   a deployable member coupled with the stent body and configured to hinge from inside of the stent body, align with an outer surface of the stent body after hinging from the inside of the stent body, and increase a body lumen contact surface area of the stent, wherein the deployable member is configured to hinge from inside of the stent body to outside of the stent body to increase the body lumen contact surface area of the stent.

2. The stent of claim 1, wherein the deployable member is configured to extend in length axially in a direction away from the stent body.

3. The stent of claim 1, wherein the deployable member comprises at least one flap hingedly coupled with the stent body and configured to hinge from inside of the stent body.

4. The stent of claim 1, wherein the deployable member comprises a plurality of flaps hingedly coupled with the stent body and equidistantly spaced around a circumference of the stent body, wherein the plurality of flaps are configured to hinge from inside of the stent body.

5. The stent of claim 1, wherein the deployable member is sized to cover a body lumen access hole of a body lumen through which the stent accessed the body lumen.

* * * * *